US012564511B2

(12) United States Patent
Brönnimann et al.

(10) Patent No.: US 12,564,511 B2
(45) Date of Patent: Mar. 3, 2026

(54) LID FOR AN OSTOMY IMPLANT

(71) Applicant: OSTOMYCURE AS, Oslo (NO)

(72) Inventors: Benedict Brönnimann, Penthaz (CH);
Mats Erik Kindahl Cardell,
Sollentuna (SE); Erik Elwing,
Jonkoping (SE); Kristoffer Apelstedt,
Jonkoping (SE); Daniel Abrahamsson,
Mullsjo (SE)

(73) Assignee: OSTOMYCURE AS, Oslo (NO)

( * ) Notice: Subject to any disclaimer, the term of this
patent is extended or adjusted under 35
U.S.C. 154(b) by 0 days.

(21) Appl. No.: 18/314,882

(22) Filed: May 10, 2023

(65) Prior Publication Data

US 2023/0277359 A1 Sep. 7, 2023

Related U.S. Application Data

(62) Division of application No. 17/046,767, filed as
application No. PCT/EP2019/058671 on Apr. 5,
2019, now Pat. No. 11,679,018.

(30) Foreign Application Priority Data

Apr. 12, 2018 (GB) ...................................... 1806045

(51) Int. Cl.
*A61F 5/44* (2006.01)
*A61F 5/442* (2006.01)
(52) U.S. Cl.
CPC ............ *A61F 5/4407* (2013.01); *A61F 5/442*
(2013.01)

(58) Field of Classification Search
CPC ...... A61F 2005/4455; A61F 5/441–445; A61F
5/448; A61F 5/44–449; A61F 5/449
See application file for complete search history.

(56) References Cited

U.S. PATENT DOCUMENTS 4,634,421 A 1/1987 Hegemann
5,026,360 A 6/1991 Johnsen et al.
(Continued)

FOREIGN PATENT DOCUMENTS

CN 103476369 A 12/2013
CN 104890996 A 9/2015
(Continued)

OTHER PUBLICATIONS

Midstate Mold. The Difference Between Double Shot Molding and
Overmolding [online]. [retrieved on Sep. 26, 2024]. Retrieved from
the Internet: <URL: https://www.midstatemold.com/difference-
between-double-shot-molding-and-overmolding/> (Year: 2018).*
(Continued)

*Primary Examiner* — Nicholas J. Weiss
*Assistant Examiner* — Linnae E. Raymond
(74) *Attorney, Agent, or Firm* — Dinsmore & Shohl LLP

(57) ABSTRACT

A lid for an ostomy implant is provided. A base includes an
attachment means for attachment to the implant and a sliding
part. The sliding part is arranged such that when the sliding
part is slid along a first sliding route, the sliding part causes
the lid to be attachable to or detachable from the implant,
and when the sliding part is slid along a second sliding route,
the sliding part causes the lid to open, for evacuating a stoma
to which the ostomy implant is connected, and closed, for
preventing leaks from the stoma, while the lid remains
attached to the implant.

9 Claims, 22 Drawing Sheets

(56)                References Cited

U.S. PATENT DOCUMENTS

| | | | |
|---|---|---|---|
| 5,045,052 | A | 9/1991 | Sans |
| 5,248,308 | A | 9/1993 | von Emster |
| 5,269,774 | A | 12/1993 | Gray |
| 5,693,036 | A * | 12/1997 | Kilgour ............... B29C 45/4407 |
| | | | 604/338 |
| 6,033,390 | A | 3/2000 | von Dyck |
| 6,537,261 | B1 * | 3/2003 | Steer ....................... A61F 5/448 |
| | | | 604/342 |
| 2003/0220621 | A1 | 11/2003 | Arkinstall |
| 2004/0184876 | A1 * | 9/2004 | Hessel ................... A61F 5/448 |
| | | | 403/326 |
| 2012/0245535 | A1 | 9/2012 | Jacobsson et al. |
| 2013/0030397 | A1 | 1/2013 | Sabeti |
| 2013/0304008 | A1 | 11/2013 | Hanuka et al. |
| 2014/0114266 | A1 | 4/2014 | Arcand |
| 2015/0141944 | A1 * | 5/2015 | Hanuka ................... A61F 5/442 |
| | | | 604/338 |
| 2016/0030227 | A1 * | 2/2016 | Brönnimann ........... A61F 5/445 |
| | | | 604/338 |

FOREIGN PATENT DOCUMENTS

| | | | |
|---|---|---|---|
| CN | 102421395 | A | 4/2021 |
| EP | 0482104 | B1 | 9/1994 |
| EP | 0737456 | A2 | 10/1996 |
| EP | 0737458 | A2 * | 10/1996 |
| EP | 0865779 | A1 * | 9/1998 |
| EP | 1652497 | A1 | 5/2006 |
| EP | 2615462 | A1 | 9/2015 |
| EP | 2915462 | A1 | 9/2015 |
| GB | 2511825 | A | 9/2014 |
| JP | 04189351 | A | 7/1992 |
| JP | 10192319 | A | 7/1998 |
| WO | 2001049224 | A1 | 7/2001 |
| WO | 2001049225 | A1 | 11/2001 |
| WO | 2003013404 | A1 | 2/2003 |
| WO | WO-2005048892 | A2 * | 6/2005 ............ A61F 5/445 |
| WO | 2006046210 | A1 | 5/2006 |
| WO | 2007059774 | A1 | 5/2007 |
| WO | 2009056906 | A1 | 5/2009 |
| WO | WO-2011039517 | A1 * | 4/2011 ............ A61F 5/445 |
| WO | 2011138727 | A1 | 11/2011 |
| WO | 2011138731 | A2 | 11/2011 |
| WO | WO-2012131351 | A2 * | 10/2012 ............ A61F 5/445 |
| WO | 2017079532 | A1 | 5/2017 |
| WO | 2017216302 | A2 | 12/2017 |

OTHER PUBLICATIONS

Chinese Office Action corresponding to CN App. No. 201980025042.1 issued May 6, 2023, 19 pages.

Search Report from IPO, GB Application No. Application No. 1806045.9, dated Nov. 10, 2018.

Second Searct1 Report from IPO, GB Application No. Application No. 1806045.9, dated Nov. 3, 2019.

International Search Report and Written Opinion, PCT/EP2019/058671, dated Jun. 24, 2019.

* cited by examiner

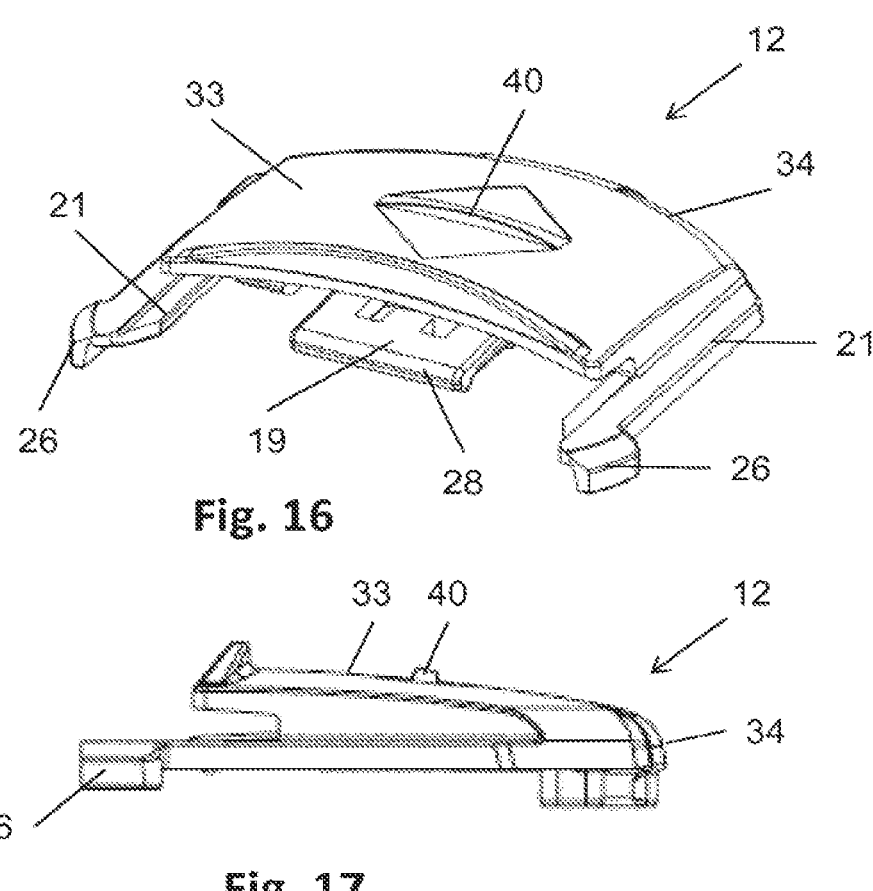
Fig. 16
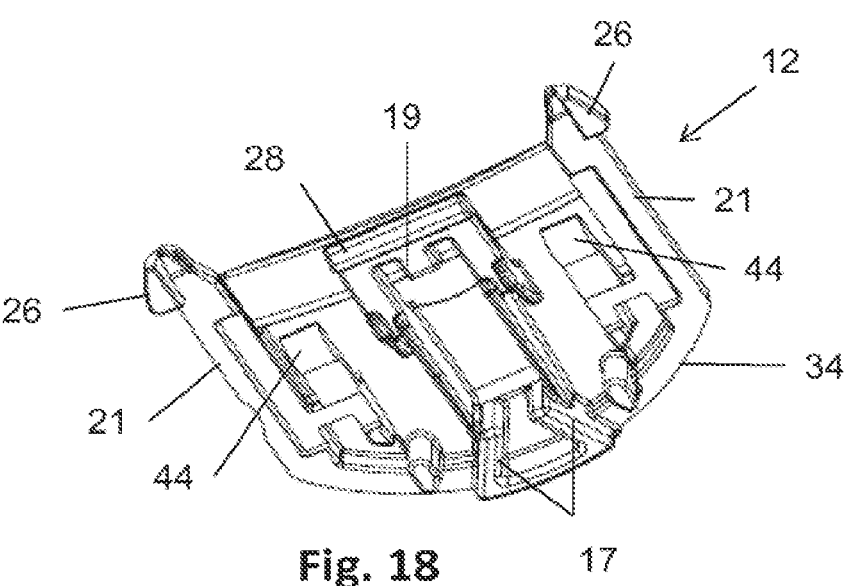
Fig. 17
Fig. 18

13'

13a

13b'

13c

38'

1

LID FOR AN OSTOMY IMPLANT

CROSS-REFERENCE TO RELATED APPLICATIONS

The present application is a divisional application of U.S. patent application Ser. No. 17/046,767 filed Oct. 9, 2020, which is a U.S. National Stage filing of International Patent Application No. PCT/EP2019/058671 filed Apr. 5, 2019, which claims the priority benefit of British Application No. 1806045.9 filed Apr. 12, 2018, the contents of each are incorporated herein by reference in their respective entireties.

BACKGROUND

The present invention relates to a lid. In particular, it relates to a lid for a medical implant, more particularly for an ostomy implant. The invention also relates to a connector for a lid for an ostomy implant or for an ostomy implant.

Ileostomy and colostomy are common operations which may be necessitated, for example, by malignancy or chronic bowel inflammation. The surgery is called an ileostomy if the colon and rectum are removed and a colostomy if the rectum alone is removed. Similarly an abdominal urostomy is created when the urinary bladder has to be removed due to, for example, bladder cancer. In these operations, a stoma is formed in the abdominal wall to which a bowel segment is connected.

Ostomy is a generic term for any such procedure where a stoma is created. The stoma, in most cases, is connected to a bag for the collection of bodily waste. However, instead of a conventional ileostomy, it is possible to make a reservoir known as a "Kock's pouch" from the distal part of the ileum. The pouch is formed in such a way that a nipple valve is created which serves to close the reservoir, whilst allowing it to be drained intermittently by means of a catheter. This is an example of a so-called continent ileostomy (CI) and it was formerly an attractive alternative to conventional ileostomy but is now rarely used. The complexity of the procedure and the high potential for complications-most of them related to dysfunction of the continence nipple valve—has deterred many surgeons from adopting the operation today.

The ileopouch anal anastomosis (IPAA) is today the gold standard worldwide for these patients but, as with a CI, this operation is also risky and failures are common, mostly leading to pouch excision with loss of bowel. Con-version of a failed IPAA to a CI would be a preferable option but, again, surgeons are reluctant to perform this complex and unreliable technique. Likewise, conversion of a mal-functional orthotopic neobladder or Bricker urostomy would be desirable.

It is known to provide an implant to facilitate connection of a stoma to a lid or bag, for example.

For example, and as illustrated in FIGS. 1 and 2, the applicant's earlier application WO 2014/140344 A1 discloses a percutaneous ostomy implant 1 comprising a tubular interior section 2, which is formed mainly of mesh, and a circular, radially-extending anchoring flange or dermal anchor 3.

The implant 1 is designed to be implanted through the abdominal wall of a patient and to receive a bowel section drawn through it. Serosal tissue from the bowel section can then grow into the implant 1, through the mesh, and attach or grow into surrounding dermal tissue. This can provide a secure, stable, leak-proof and well-vascularised tissue-implant junction.

The tubular interior section 2 is attached to an exterior section 4, which, when the implant 1 is implanted in a patient, protrudes from the patient's body. A groove 6 around the exterior circumference of the exterior section 4 allows a lid, bag or other device (not shown) to be attached to the implant 1.

Once an implant has been implanted into a patient, it is necessary to close it in some way, or to sealingly connect it to some form of evacuation means (e.g. a bag, sleeve or catheter), to prevent leakage of waste from the stoma, and to allow waste to be collected and/or disposed of cleanly. This means that usually some form of lid or bag needs to be attached to the external end of the implant.

The applicant's earlier application WO 2006/046210 A1 discloses a detachable lid for an implant with mounting means (e.g. a groove or ridge) arranged such that the detachable lid can be mounted onto and removed from an external end of the implant by sliding the lid in a direction perpendicular to the longitudinal axis of the implant.

However, a problem with this method of mounting a lid on an implant is that it may cause forces to be exerted on the implant which can damage the tissue-implant junction. It can also be difficult for a patient to mount a lid in this way.

A further problem is that with this sliding method of attachment, it may be difficult for the lid to seal properly, i.e. in a leak-tight way, with the implant.

WO 2006/046210 A1 also discloses a connecter for connecting an ostomy bag to the implant. The connector is arranged to slide the lid off of the implant and to connect the bag to the implant.

In the applicant's later application WO 2011/039517 A1, a medical closure device is disclosed comprising a coupling part and a closure part (e.g. a lid or cap). The coupling part can be attached to a medical device such as an implant and the closure part can then be attached to the coupling part to close the implant. The coupling part is a circumferential flexible member delimiting a coupling opening, and is configurable between a relaxed configuration where the coupling opening cannot pass over the medical device and a stressed configuration where the coupling opening of the coupling part can pass over the medical device. Thus, if the coupling part is squeezed, it will deform from its relaxed configuration into a stressed configuration in which it can be passed over the end of the implant. When pressure is released (i.e. the squeezing is stopped), the coupling part will attempt to return to the relaxed configuration, thus gripping the end of the implant. The reverse procedure can be performed to remove the coupling part.

However, a problem with the coupling part of WO 2011/039517 A1 is that it may be possible for the coupling part to become detached from the implant, unintentionally or accidentally, for example if, e.g. by leaning on an object, pressure is applied to the coupling part causing it to be squeezed into its stressed configuration whereby it may become detached from the implant.

The closure device of WO 2011/039517 A1 is also relatively wide and, when attached to an implant, extends down close to the patient's skin such that there is a risk of abrasion and irritation.

Attaching the closure part of WO 2011/039517 A1 to the coupling part of WO 2011/039517 A1 requires two hands, which may be problematic for a user. Also, as the closure device comprises two separate parts (the coupling part and the closure part) there is greater chance of one part becoming lost or dropped, compared with a closure device made of a single part. Handling may also be more inconvenient.

Furthermore, there is a possibility with this closure device that it could become attached to the implant (locked) in an incorrect position, such that it is not properly seated and sealed on the implant. For example, often a user cannot see the lid-implant interface (e.g. due to clothing or stomach being in the way) and so they may attach or lock the closure device onto the implant in an incorrect position.

The applicant's more recent application WO 2017/216302 A2 discloses a lid for a medical implant, the lid comprising a first part, a second part and engaging means, wherein the second part is rotatable relative to the first part (or the first part is rotatable relative to the second part) such that, in use, rotation of the second part relative to the first part (or vice versa) causes the engaging means to engage with and attach the lid to the implant.

SUMMARY

According to an aspect of the invention, there is provided a lid for an ostomy implant, the lid comprising:

attachment means for attachment to the implant; and an opening part;

wherein the opening part is arranged such that it can be opened and closed while the lid is attached to the implant.

The lid comprises an opening part which can be opened and closed while the lid is attached to the implant. This means that waste may be evacuated from a stoma to which the ostomy implant is connected (preferably through an opening created/opened by opening the opening part) whilst the lid is still attached to the implant, as the opening part in the lid may be opened for this purpose, without having to detach the lid. As the lid does not first have to be taken off of the implant before evacuation, emptying of the stoma can be performed more straightforwardly and with less mess. Once the stoma has been evacuated, the opening part may then be closed again, e.g. to prevent any leaks until the user is ready to next empty the stoma.

Preferably, the opening part is or comprises a hatch. Thus, the hatch in the lid may be opened to allow the stoma to be evacuated. A hatch is preferably an opening part which opens by pivoting upwards (i.e. away) from the rest of the lid. Alternative kinds of opening parts could also be used, e.g. which open in different ways such as by twisting, turning or sliding.

The lid preferably comprises an operating means, wherein the operating means is operable to: allow the lid to be attached to or detached from the implant; and/or open and/or close the opening part. In a preferred embodiment the operating means is operable (e.g. in different ways) both to allow the lid to be attached to or detached from the implant and to open and/or close the opening part.

The operating means may be arranged such that when it is operated in a first way it allows the lid to be attached to or detached from the implant, and when it is operated in a second way it opens and/or closes the opening part. The first way of operation and the second way of operation are preferably different. For example, the operating means may be arranged such that when it is operated in a first way it puts the lid into a configuration in which it may be attached to or detached from the implant. When the operating means is operated in a second way, this may cause the opening part to open and/or close.

The operating means may, for example, comprise a sliding part (e.g. a slider). Operating the operating means may comprise sliding the sliding part.

The sliding part may be arranged such that when the sliding part is slid along a first sliding route, it may cause the opening part to open or close. Additionally or alternatively, in some embodiments, the sliding part is further arranged such that when the sliding part is slid along a second sliding route it causes the lid to be attachable to or detachable from the implant. The first and second sliding routes are preferably different. They may, for example, be collinear.

In a preferred embodiment, from a first state (sliding part position) in which the opening part is closed, sliding the sliding part in a first direction may cause the opening part to open. Sliding the sliding part back again, in the opposite direction, may then cause the opening part to close.

In some embodiments, additionally or alternatively, from the same first state (sliding part position), e.g. in which the lid is (also) not attachable to or detachable from the implant, sliding the sliding part in, e.g., the opposite direction to the first direction, may cause the lid to be changed into a configuration (e.g. a stressed configuration) in which the lid is attachable to or detachable from the implant. Sliding the sliding part back again to the first state (sliding part position) may cause the lid to be changed into a configuration (e.g. a relaxed or less stressed configuration) in which the lid is no longer attachable to or detachable from the implant (although it may be, and in some cases prefer-ably is, attached to the implant at this point).

In an alternative embodiment, the lid (e.g. its operating means) may comprise a lever part. This may be an alternative to the sliding part or in addition to the sliding part. In some preferred embodiments, the slider part and the lever part may be the same component, i.e. the slider/lever part can act as both/either a slider or a lever. In such cases, it may be necessary for the opening part to be open in order for the slider/lever part to act as a lever.

The lever part is preferably arranged such that when it is moved or operated in a first direction or way, it causes the lid to be changed into a configuration (e.g. a stressed configuration) in which the lid is attachable to or detachable from the implant. Preferably, when the lever is moved in a second direction or way, which is preferably opposite to the first direction or way, this causes the lid to be changed into a configuration (e.g. a relaxed or less stressed configuration) in which the lid is no longer attachable to or detachable from the implant (although it may be, and in some cases prefer-ably is, attached to the implant at this point).

Preferably, the lever part is arranged such that it can be moved in a circumferential direction around a circumference of the lid. Alternatively, it may be moved in a twisting or tilting motion.

Preferably, moving the lever part in the first direction or way causes the lid, or part of the lid (e.g. the base or part of the base described below) to be flexed and/or stretched, thereby causing the lid to be changed into a configuration (e.g. a stressed configuration) in which the lid is attachable to or detachable from the implant.

Preferably, moving the lever part in the second direction or way (or simply reducing or removing a force acting on the lever part such that the lever part moves in the second direction or way) causes the lid, or part of the lid (e.g. the base or part of the base described below) to change into a configuration (e.g. a relaxed or less stressed configuration) in which the lid is no longer attachable to or detachable from the implant (although it may be, and in some cases prefer-ably is, attached to the implant at this point).

Preferably, changing the lid into a configuration (e.g. a stressed configuration) in which the lid is attachable to or detachable from the implant comprises enlarging an opening in the lid (e.g. such that it can fit over the implant).

Preferably, changing the lid into a configuration (e.g. a relaxed or less stressed configuration) in which the lid is no longer attachable to or detachable from the implant comprises reducing the size of an opening in the lid (e.g. such that it cannot fit over the implant).

The operating means (e.g. the sliding part or lever part) preferably comprises a surface or protrusion arranged such that when the operating means is operated, the surface or protrusion exerts a force on another part of the lid (e.g. a base, as described below, for example), e.g. so as to change the lid into a configuration (e.g. a stressed configuration) in which the lid is attachable to or detachable from the implant, for example, and preferably, by enlarging an opening in the lid (e.g. such that it can fit over the implant).

The surface or protrusion of the operating means may, for example, comprise one or more angled parts or members. The lid preferably comprises one or more further surfaces or protrusions (e.g. angled parts or members) arranged such that the surface or protrusion of the operating means can exert a force on the one or more further surfaces or protrusions of the lid (e.g. in a base, as described below, for example), so as to change the lid into a configuration (e.g. a stressed configuration) in which the lid is attachable to or detachable from the implant, for example, and preferably, by enlarging an opening in the lid (e.g. such that it can fit over the implant). The angled parts of members preferably extend radially inwardly, e.g. from a radial edge of the operating means, and/or preferably towards each other.

The lid preferably further comprises connection means such that a further device may be attached to the lid. The further device could be a connector, ostomy bag, catheter, or irrigation sleeve, for example. The connection means may comprise one or more raised or lowered parts such as a ridge, bump, indentation and/or groove, for example. Alternatively or additionally, the connection means may comprise a magnet or magnetic part, e.g. for connection to a magnetic part or magnet on a further device. The attachment means is preferably provided around a circumference of the lid. Other connection means would of course also be possible. The connection means may be provided in, and preferably around a circumference of, a base (as described below) of the lid, for example.

The further device may have, and preferably does have, its own connection means which can be attached to the connection means of the lid.

The connection means provided on the further device preferably correspond to or are arranged to cooperate and connect with/attach to the connection means provided on the lid.

In an example, the connection means of the further device may comprise a suction part, e.g. a suction ring (ring-shaped suction part), e.g. for connection with a smooth and/or polished (preferably side) surface on the lid. The suction ring could, for example, comprise two concentric rings with a vacuum being formed therebetween, e.g. along a concentric disc segment, preferably around a complete circumference (360 degrees). The suction ring is preferably arranged, and/or has a sufficiently large inner diameter, such that it does not (cannot) suck out any content from a stoma when the opening part is opened.

In such cases, the connection means provided on the lid would be the smooth and/or polished (preferably side) surface on the lid.

By providing such connection means on the lid (and further device), this means that such further devices may be attached to the lid and do not, for example, need to be attached to a patient's skin (which can cause problems such as irritation, soreness or inflammation). The provision of connection means on the lid, e.g. in an appropriate location, can also distance such further devices from the patient's skin, which also helps to prevent any irritation they may cause when attached.

Furthermore, such further devices may be attached to the implant via the lid without having to first remove the lid. In the case of irrigation sleeves, catheters or ostomy bags, for example, this can be particularly advantageous as the opening part of the lid may be opened, e.g. through the sleeve or bag, after the sleeve or bag has been (sealingly) connected to the lid, so that evacuation of the stoma can be performed without the possibility of soiling of a user's hands, for example.

The lid comprises attachment means for attachment to the implant. The attachment means preferably comprises an edge or protrusion for engagement with the implant. Alternatively or additionally, the attachment means may comprise an indentation or groove, for example, for engagement with a raised part on the implant. Other examples of possible attachment means include a magnet, a magnetic part, a suction part (e.g. a suction ring (ring-shaped suction part), e.g. for connection with a smooth and/or polished (preferably side) surface on the implant). Other attachment means are of course also possible.

Preferably, the attachment means is arranged to attach to an outer, e.g. radially outer, surface or part of an implant.

Preferably, the attachment means is also or alter-natively arranged to attach to an exterior part of an implant. An exterior part of an implant may be a part of the implant which, when the implant is implanted in a patient, is outside of the patient (outside of the patient's body).

The attachment means preferably comprises a seal or sealing surface for sealing engagement with the implant. For example, the attachment means may be formed, or partly formed, of a soft (e.g. rubbery) and/or flexible sealing material.

The lid is preferably operable between a relaxed (or less stressed) configuration in which it cannot fit over the implant, and a stressed (e.g. partly squeezed and/or stretched) configuration in which it can fit over the implant. Thus, once the lid has been fitted over the implant, it may (be allowed to) return to its relaxed configuration (e.g. by stopping or reducing a force acting on a component of the lid) such that it is attached to the implant and cannot be removed until it is placed in the stressed configuration again.

The lid preferably comprises a sealing surface (or sealing component) for sealing engagement with the implant. This means that when the lid is attached to the implant, it can be in sealing engagement with it, thereby preventing leaks. The sealing surface is preferably at least partly ring-shaped so as to provide a seal around the circumference of the implant.

The lid preferably comprises a sealing surface (or sealing component) for sealing engagement with the opening part (e.g. when it is closed). This means that when the opening part is closed, it can be in sealing engagement with the rest of the lid (e.g. a base) such that waste from the stoma is prevented from leaking while the lid is closed and attached to the implant.

The sealing surface for sealing engagement with the implant and the sealing surface for sealing engagement with the opening part may be (and in a preferred embodiment are) provided by a same sealing component, e.g. a sealing ring. Thus, the sealing component is preferably arranged such that it (e.g. its sealing surfaces) can form a seal between the implant and the opening part.

The lid preferably comprises a base to which the opening part is, e.g. movably, connected. The base preferably comprises (or has connected thereto) the attachment means for attachment to the implant.

The base may comprise at least one stretchable part. The stretchable part may, for example, comprise one or both of the sealing surfaces (e.g. the sealing component or components) referred to above.

The stretchable part may be formed of a soft and flexible plastic or rubber material.

The base, e.g. the, or including the, stretchable part, is preferably stretchable from a relaxed (or less stressed) configuration in which it cannot fit over the implant, to a stressed configuration in which it can fit over the implant.

The lid, e.g. its base, preferably comprises (or forms) an opening which is or can be closed by the opening part. Preferably, the opening is an opening through which waste may pass when the lid is attached to the implant (and, e.g., the opening part is open).

Stretching the lid, e.g. its base, or a stretchable part of the base, or placing it in a stressed configuration may comprise or result in enlarging the opening such that it can fit over the implant.

The lid or base preferably comprises a stretchable part and at least one less stretchable part which is less easily stretched (e.g. is relatively more rigid) than the stretchable part. The less stretchable part may, for example, comprise a gap such that it may be bent or flexed in order to enlarge the opening, for example.

The base preferably comprises one or more grooves, e.g. through which the operating means (e.g. slider) can slide or move.

In a preferred embodiment, the base comprises an upper part, a middle part and a lower part.

The upper part may be substantially C-shaped (e.g. ring-shaped but with a gap in it, e.g. in/through which a slider can fit or slide).

The lower part may be generally ring-like shape but preferably with a gap in it, breaking its circumference.

The middle part may, for example, be the stretch-able part. The middle part may be located, for example, at least partly between the upper and lower parts. The middle part may comprise an upper middle part and a lower middle part. The upper middle part may be located, for example, at least partly between the upper and lower parts. The lower middle part may be located, for example, beneath the upper parts. The middle part (e.g. the lower middle part) may fill a gap in the lower part.

A preferably circular opening is preferably formed in the base, preferably in its middle part. The upper and/or lower parts preferably (only) partly surround the opening.

The upper and lower parts are preferably more rigid than the middle part.

The base (e.g. the bottom part, preferably comprises a recess or groove in which an axel of the opening part may sit and rotate.

The base preferably comprises or forms an opening which is preferably delimited by a soft flexible edge, e.g. of the middle part.

The operating means (e.g. the sliding part and/or lever part) may be operable to apply a force on the lid (e.g. on the base) so as to enlarge the opening so that it can fit over the implant.

The operating means (e.g. the sliding part and/or lever part) may additionally or alternatively be operable so as to apply a force on the opening part so as to open or close the opening part, and/or to keep the opening part open or closed.

The operating means could be, and preferably is, a movable part (e.g. a part which is movable with respect to the rest of the lid).

Preferably, the lid is substantially circular (e.g. when viewed from above or below) or cylindrical.

In a preferred embodiment, the opening and/or the opening part are not positioned centrally in the lid.

In a preferred embodiment, the operating means is a slider which is arranged so as to be slidable inwards and outwards in a radial direction with respect to the lid. The slider may also or alternatively be arranged such that (e.g. when it has been slid outwards in a radial direction with respect to the lid) it may be twisted or turned so as to act as a lever (e.g. to enlarge the opening).

The base preferably comprises at least one stretchable part and at least one less stretchable part, the less stretchable part preferably being substantially ring-shaped but preferably with a circumferential gap at one point.

The slider and base are preferably arranged such that when the slider is moved, e.g., radially inwards, it exerts a force on the base, causing the less stretchable part to be stretched or bent such that the circumferential gap is increased. The stretchable part is preferably also stretched. In this way, an (the) opening in the base is preferably enlarged, e.g. such that the lid can be fitted over the implant.

The slider preferably comprises a protruding member (e.g. a tongue), which preferably protrudes radially inwardly (and maybe also slightly downwards) with respect to the lid. The slider may comprise an upper part, e.g. from which the protruding member extends, preferably beneath.

The slider, e.g. its protruding member, may comprise an engagement part (e.g. a hook) for engagement with the opening part (e.g. its projection, as described below).

The slider (or other operating means) may comprise one or more gripping means, e.g. on an upper surface thereof. The gripping means could comprise one or more raised and/or lowered surfaces (e.g. with respect to the rest of the slider or other operating means), for example. The gripping means can assist in sliding the slider or otherwise operating the operating means.

The slider preferably comprises one or more ridges, e.g. along opposite sides in a sliding direction. The ridges are preferably arranged for sliding through the rest of the lid (e.g. through grooves provided, for example, in a base of the lid).

An engaging member may be provided at the end of each ridge, or elsewhere on the slider, for example, for engaging with a part of the rest of the lid (e.g. in its base). Such engaging members could prevent the slider from being slid completely out of the rest of the lid.

The slider (e.g. its protruding member) and the opening part are preferably arranged such that when the slider is moved, e.g. radially outwards, the slider (e.g. its protruding member) exerts a force on the opening part, thereby causing the opening part to open and, preferably, then be held in an open position. Preferably, the slider and opening part are further arranged such that when the slider is moved back, e.g. radially inwardly, the slider (e.g. its protruding member) exerts a force on the opening part, thereby causing the opening part to close and, preferably, then be held in a closed position.

The opening part preferably comprises a projection arranged such that, in use, the slider (e.g. its protruding member) exerts a force (e.g. as described above) on the projection of the opening part.

The opening part may comprise an opening end and a pivoting end.

The projection is preferably located at a pivoting end of the opening part. The projection of the opening part and the protruding member of the slider are preferably arranged such that when the protruding member exerts a force on the projection causing it to move downwards, this causes the opening end of the opening part to move upwards, thereby causing the opening part to open.

Preferably, when the opening part is closed, the projection projects upwardly. Preferably, when the opening part is open, the projection projects more radially outwardly from the lid (but still, e.g., slightly upwardly).

The opening part preferably comprises a top part and a bottom part. The top part and the bottom part may be connected or joined solely at the opening end of the opening part, for example. Preferably, there is a recess or space between the top part and the bottom part. Preferably, the top part may be bent or flexed towards the bottom part, e.g. when a force is applied to it.

The opening part preferably comprises an axel, e.g. at its pivoting end. The axel is preferably arranged horizontally, e.g. such that the opening part can open upwardly by pivoting via the axe.

The slider, e.g. and preferably its protruding member, is preferably arranged such that it can be slid (or partly slid) between the top part and the bottom part of the opening part.

The slider, e.g. and preferably its upper part, is preferably arranged such that it can be slid (or partly slid) over the opening part (e.g. and preferably its top part).

Preferably, the lid is provided separately from the implant, e.g. there is no physical connection between the lid and the implant and the lid may be completely detached from implant (e.g. without breaking any physical connection) when removed from/not covering the implant.

A connector is provided for connection to an ostomy implant or to a lid for an ostomy implant, the connector comprising attachment means for attachment to the ostomy implant or lid, and connecting means or a connection surface for connection to (or connected to) a further device.

By providing such a connector, an implant or lid may be easily connected to further devices. The further devices could be an ostomy bag, a catheter (for flushing and/or emptying), or an irrigation sleeve, for example.

The connection surface preferably comprises a relatively planar surface, e.g. for attachment to a further device such as a sleeve, bag or catheter. A sleeve, bag or catheter (or other device) could be attached to the connection surface for example with an adhesive. Other attachment means for attaching a further device to the connector may include a tapered nozzle, a luer connection and a bayonet lock, for example. Other attachment means could alternatively be used.

The connector preferably comprises a seal, e.g. a sealing ring or part(s), for sealing engagement with the ostomy implant or lid. This can help to prevent leaks, e.g. when evacuating a stoma.

The connector is preferably substantially ring-shaped, or comprises or forms a substantially ring-shaped part or region, e.g. such that it can connect to the lid or implant around the circumference of the lid or implant. This can help to improve the secureness of the connection and provide a larger surface to which, e.g. a bag, catheter or sleeve may then be attached, without any gap.

Preferably, the connector is formed of one or more parts which are not movable with respect to each other. For example, the connector may comprise a ring with a flexible inner part. The flexible inner part is preferably arranged (e.g. sized and dimensioned) for (e.g. sealing) engagement with the lid or implant. Preferably an outer part of the ring is less flexible than the flexible inner part. Although the flexible inner part can flex slightly, the relative positions of the flexible inner part and the less flexible outer part cannot change, i.e. the flexible inner part and the less flexible outer part are fixedly connected to each other.

Preferably, the less flexible outer part comprises one or more tongues which project radially inwardly into, through, over, and/or under the flexible inner part. The one or more tongues are preferably less flexible than the flexible inner part. For example, they may be, and preferably are, made of the same material as the less flexible outer part.

Alternatively, the connector may comprise two or more moveable parts, the two or more moveable parts being movable between a, for example, stressed, configuration in which they can be placed over the lid or implant, and a, for example, relaxed, configuration in which they are connected to the lid or implant.

The connector may be made of one or more plastics materials such as polypropylene and/or Mediprene®. In a preferred embodiment, the less flexible outer part (and optionally also its tongues) is (are) preferably made of polypropylene and the flexible inner part is preferably made of Mediprene®.

The present invention also relates to a lid as described above with a connector as described above attached thereto.

Preferably, when the connector is connected to the lid, the opening part can be opened and closed.

Preferably, when the connector is connected to the lid, the lid cannot be placed in the, e.g. stressed, configuration in which the lid can be removed from the implant.

The present invention also relates to a system for evacuation of a stoma, the system comprising a lid as described above and a connector as described above, wherein the connector is connectable to (or connected to) the lid. The system may also comprise an ostomy implant, the lid and/or connector preferably being connectable to (or connected to) the implant. The system may also comprise a further device such as an irrigation sleeve, catheter and/or ostomy bag, the further device preferably being connectable to or connected to the connector.

The present invention also relates to a kit comprising a lid as described above and one or more connectors as described above, wherein the one or more connectors are connectable to the lid. The kit may also comprise a further device, such as an irrigation sleeve, catheter and/or ostomy bag, the further device preferably being connectable to or connected to the connector.

The present invention also relates to an ostomy implant with a lid as described above attached thereto.

The present invention also relates to an ostomy implant with a connector as described above attached thereto.

The present invention also relates to an ostomy bag with a connector as described above attached thereto.

The present invention also relates to an irrigation sleeve with a connector as described above attached thereto.

The present invention also relates to a catheter with a connector as described above attached thereto.

The present invention also relates to an ostomy bag comprising a connector as described above.

The present invention also relates to an irrigation sleeve comprising a connector as described above.

The present invention also relates to a catheter comprising a connector as described above.

In the case of a device (e.g. an ostomy bag, an irrigation sleeve, or a catheter) comprising a connector as described above, the connector is preferably an integral part of the device. For example, the device may be provided with the connector as a part of the device, and not, for example, for separate/subsequent attachment to the device. Such devices preferably therefore do not comprise a plate for adhesion (e.g. to a patient's skin), as is currently typically provided on such devices. Rather, the device comprises, and is preferably manufactured with, an integral connector (or connection means) for connection to the lid and/or implant.

The present invention also relates to a method of evacuating a stoma, wherein the stoma is attached to an ostomy implant, the method comprising:

attaching a lid to the implant, the lid comprising an opening part;

opening the opening part; and evacuating the stoma.

The lid is preferably as described above.

Attaching a lid to an implant may comprise operating an operating means of the lid (e.g. a slider) to place the lid in a stressed configuration in which it can be placed over the implant, placing the lid over the implant. Placing the lid over the implant may comprise attaching an attachment means on the lid to a corresponding or cooperating attachment means on the implant. The operating means may then be further operated (or allowed to move) such that the lid is placed in a (more) relaxed configuration in which the lid (e.g. its attachment means) cannot be removed from the implant (e.g. its attachment means).

The method may also comprise attaching a connector to the lid before opening the opening part. The connector is preferably as described above.

A further device, such as an ostomy bag, catheter or irrigation sleeve, may be attached to the connector.

The method may comprise attaching a further device, such as an ostomy bag, catheter or irrigation sleeve, to the connector.

The method preferably comprises opening the opening part through the further device (e.g. ostomy bag or irrigation sleeve).

If the further device is or comprises a catheter (or other such device), if the catheter (or other such device) is sufficiently soft, then the opening part may be opened through the catheter. If the catheter (or other such device) is stiffer, then the catheter (or other such device) may, for example, be twisted, rotated, bent and/or pushed downwards against the lid, thereby acting on the operating means to open the opening part. Alternatively, an operating means may be provided on the lid, next to or outside of, the catheter (e.g. next to or outside of where the catheter or other device is connected to the lid) such that is can be operated to open the opening part which the catheter (or other such device) is connected to the lid. For example, the operating means could comprise a squeezing means and/or an, e.g. rotatable, lever, which, when operated, cause the opening part to open.

The method preferably comprises evacuating the stoma into or through the further device, e.g. the ostomy bag, catheter or irrigation sleeve.

The present invention also relates to a method of attaching a lid to an ostomy implant, the lid being as described above, the method comprising attaching the lid to the implant with the attachment means.

The present invention also relates to a method of opening a lid for an ostomy implant, the lid being as described above, the method comprising opening the opening part. The lid is preferably located on (e.g. attached to) the implant.

The present invention also relates to a method of connecting a connector to a lid for an ostomy implant, the lid and the connector being as described above, the method comprising connecting the connector to the lid. The method may also comprise attaching a further device (e.g. an ostomy bag, irrigation sleeve or catheter) to the connector. Alternatively, a further device (e.g. an ostomy bag, irrigation sleeve or catheter) may already be connected to the connector. The method may comprise opening the opening part of the lid. The lid is preferably attached to an implant. The method may comprise evacuating waste from a stoma through the lid, e.g., into or through the further device.

The present invention also relates to a method of manufacturing a lid for an ostomy implant, the lid being as described above. The method may comprise manufacturing the lid by injection moulding.

The present invention also relates to a method of manufacturing a connector for an ostomy implant or for a lid for an ostomy implant, the connector being as described above. The method may comprise manufacturing the connector by injection moulding.

The present invention also relates to a method of manufacturing a further device such as an ostomy bag, irrigation sleeve and/or catheter, the further device preferably comprising (or having attached thereto) a connector as described above. The method may comprise manufacturing the further device (preferably with the connector) by injection moulding.

The lid and/or connector and/or further device may be made of one or more plastics materials such as Medical grade copolymer granules of PolyOxyMethylene, Medical grade copolymer granules of PolyButyleneTerephthalate (polyester), polypropylene and/or Medical grade elastomer granules of StyreneEthyleneButyleneStyrene.

For example, the operating means or slider may be made of POM: Medical grade copolymer granules of Poly-OxyMethylene.

The opening part may be made of PBT: Medical grade copolymer granules of PolyButyleneTerephthalate (polyester).

The base, or part of the base, (e.g. the top and bottom parts) may be made of polypropylene or ABS: Medical grade copolymer granules of AcrylonitrileButa-dieneStyrene. The base, or part of the base (e.g. the middle part) may be made of Mediprene®: Medical grade elastomer granules of StyreneEthyleneButyleneStyrene.

The lid (or its components) and/or connector and/or further device are preferably formed by injection moulding. For example, the operating means, opening part and base may each be injection moulded, then preferably assembled.

Manufacture of the lid and/or connector and/or further device (e.g. ostomy bag, catheter or irrigation sleeve, e.g. comprising a connector) is preferably performed by a controlled process and/or in a controlled environment, which is preferably clean but not (necessarily) sterile.

The base may be manufactured by first injection moulding the top and bottom parts, e.g. in separate first and second tools. These parts are then preferably inserted into a third tool, where a material (e.g. Mediprene®) is injected to both form the middle part and join the top and bottom parts (e.g. via the middle part), thereby creating the base. This process is often referred to as 2K injection moulding.

The further device (e.g. ostomy bag, irrigation sleeve or catheter) are preferably manufactured from the same material(s) as the connector. However, a different shaped tooling may be used for this, e.g. in an (e.g. 2K) injection moulding process. In some cases, a third material may be used in a 3K injection moulding process.

Alternatively, a (for example, compact) connector could be manufactured with connection means for connecting to the lid but without an e.g. large, flat surface (e.g. for connection to a further device). Instead, the connector could comprise a (preferably smaller) surface, e.g. for welding (for example by heat or ultrasonic welding) to a further device such as an ostomy bag, irrigation sleeve or catheter. Attaching the (e.g. compact) connect to a further device (e.g. by welding) can thus create a further device such as an ostomy bag, it sleeve or catheter with an integrated connector.

The further device such as an ostomy bag, irrigation sleeve or catheter could be manufactured in alternative versions e.g. without a large, for example self adhesive, plate and instead could have a small surface suitable for welding, for example, to the e.g. compact connector.

Instead of welding, other attachment methods such as use of glue or (strong) self-adhesives could be used for joining the parts.

BRIEF DESCRIPTION OF THE DRAWINGS

Embodiments of the invention will now be described with reference to the accompanying drawings, in which:

FIG. 16 is a perspective view of the top side of a slider; both form the middle part and join the top and bottom parts (e.g. via the middle part), thereby creating the base. This process is often referred to as 2K injection moulding.

FIG. 17 is a side view of a slider;

FIG. 18 is a perspective view of the bottom side of a slider;

DETAILED DESCRIPTION

Figure 1:
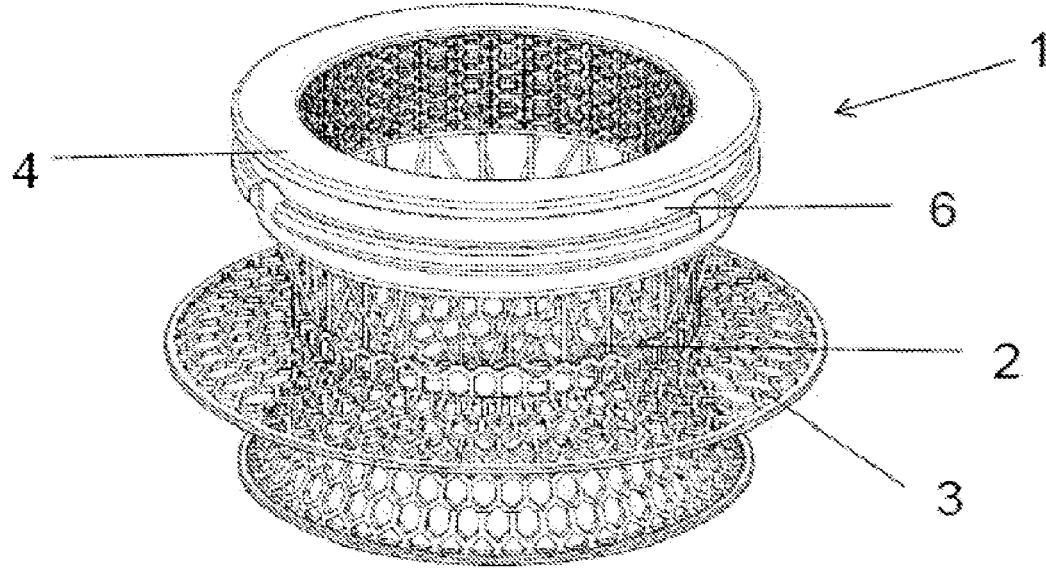
FIG. 1 is a perspective view of a known implant on which the present invention may be used.
Figure 2:
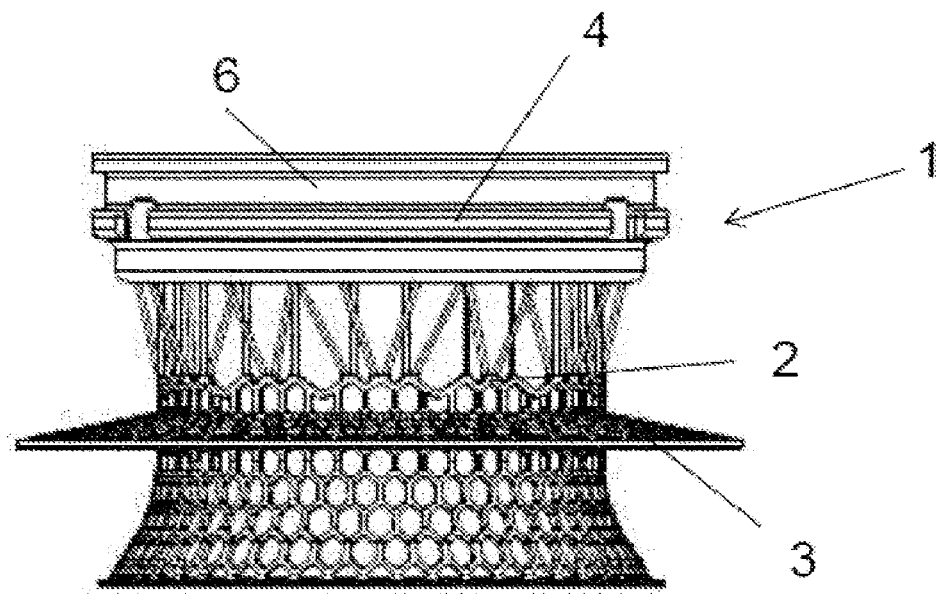
FIG. 2 is a side view of the implant of FIG. 1.

FIGS. 1 and 2 illustrate a known percutaneous ostomy implant 1 from the applicant's earlier application WO 2014/140344 A1. As described above, the implant 1 comprises a tubular interior section 2, which formed mainly of mesh, and a circular, radially-extending anchoring flange or dermal anchor 3. The tubular interior section 2 is attached to an exterior section 4, which, when the implant 1 is implanted in a patient, protrudes from the patient's body. A groove 6 around the exterior circumference of the exterior section 4 allows a lid, bag, catheter, irrigation sleeve or other device to be attached to the implant 1.

The implant 1 is designed to be implanted in the subcutaneous tissue of the abdominal wall of a patient and to receive a bowel section drawn through it.

Figure 3:
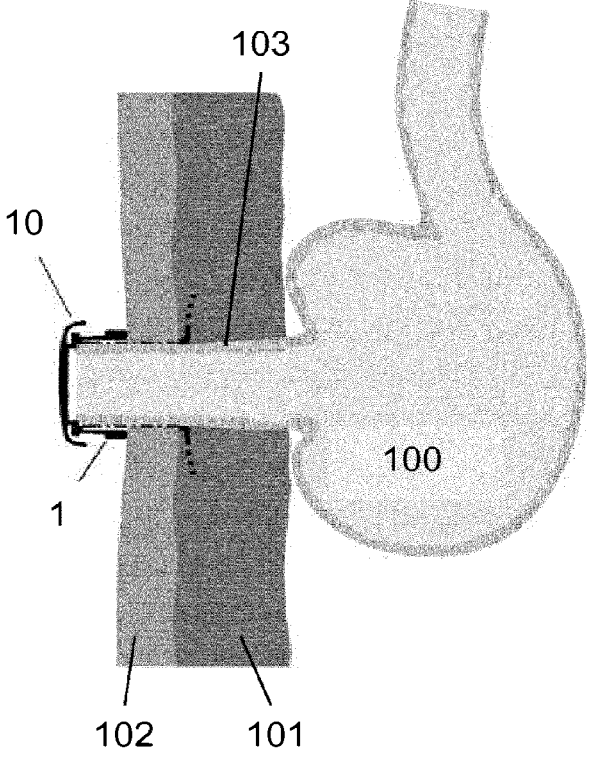
FIG. 3 is a cross-sectional view of an implant implanted in a body with a lid according to an embodiment of the invention attached thereto.

FIG. 3 is a cross-sectional view of the implant 1 implanted in a body of a patient, through the peritoneum 101 and skin 102. The patient's ileum 103 has grown into the implant 1, helping to secure the implant 1 in place. A lid 10 according to an embodiment of the invention is attached to the exterior section 4 of the implant 1. This allows the patient's bodily waste to be held in an internal reservoir 100 until the lid 10 is removed from the implant 1. The internal reservoir 100 forms in the patient's ileum after regular wearing of the lid 10 has started.

FIGS. 4(a)-(d) show an implant 1 with a lid 10 attached thereto. For the purposes of this illustration, the implant 1 is not implanted into a patient in these figures. This is merely to illustrate more clearly where, on the implant 1, the lid 10 is attached. However, in use, of course, the implant 1 would be implanted into a patient as described above with reference to FIG. 3.

As shown in FIGS. 4(a)-(d), the lid 10 is attached to the exterior section 4 of the implant 1. More specifically, the lid 10 is attached to the groove 6 around the exterior circumference of the exterior section 4. This groove 6 is not visible in FIGS. 4(a)-(d) as it is covered by the lid 10.

Figure 4:
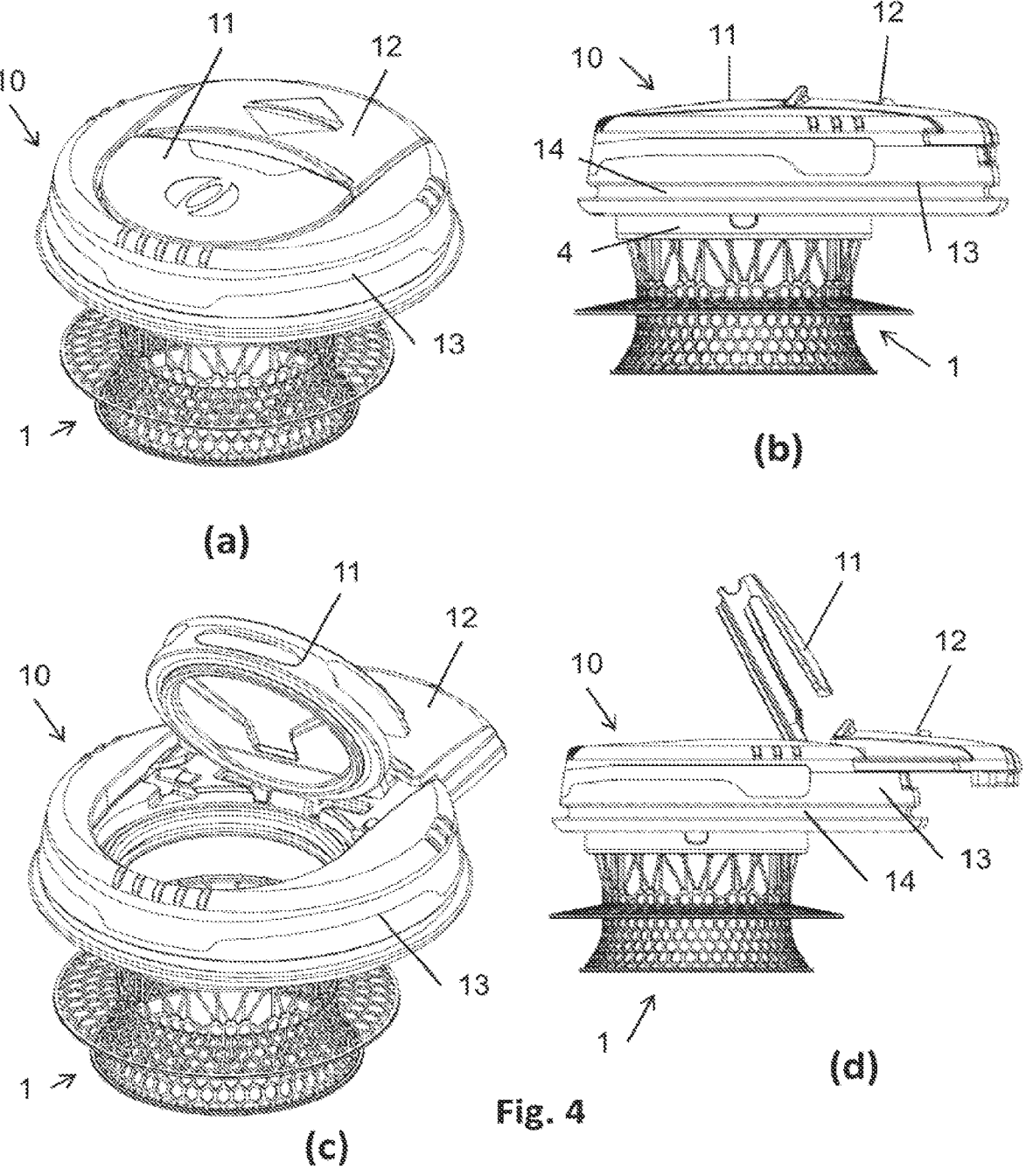
FIGS. 4 (a)-(d) show an implant with a lid according to an embodiment of the invention attached there to, where FIGS. 4 (a) and (b) show perspective and side views, respectively, with the lid closed, and FIGS. 4 (c) and (d) show perspective and side views, respectively, with the lid open.

The lid 10 has a hatch 11 which may be opened and closed whilst the lid 10 is attached to the implant 1. FIGS. 4(a) and (b) show the lid 10 with the hatch 11 in a closed configuration. FIGS. 4(c) and (d) show the lid 10 with the hatch 11 in an open configuration.

As can be seen particularly in FIGS. 4(b) and (d), although the lid 10 is circular (when viewed from above or below), it is attached to the implant 1 such that its axial centreline is not collinear with the axial centreline of the generally tubular implant 1. The lid 10 overhangs the implant 1 more on one side than on its opposite side.

Figure 5:
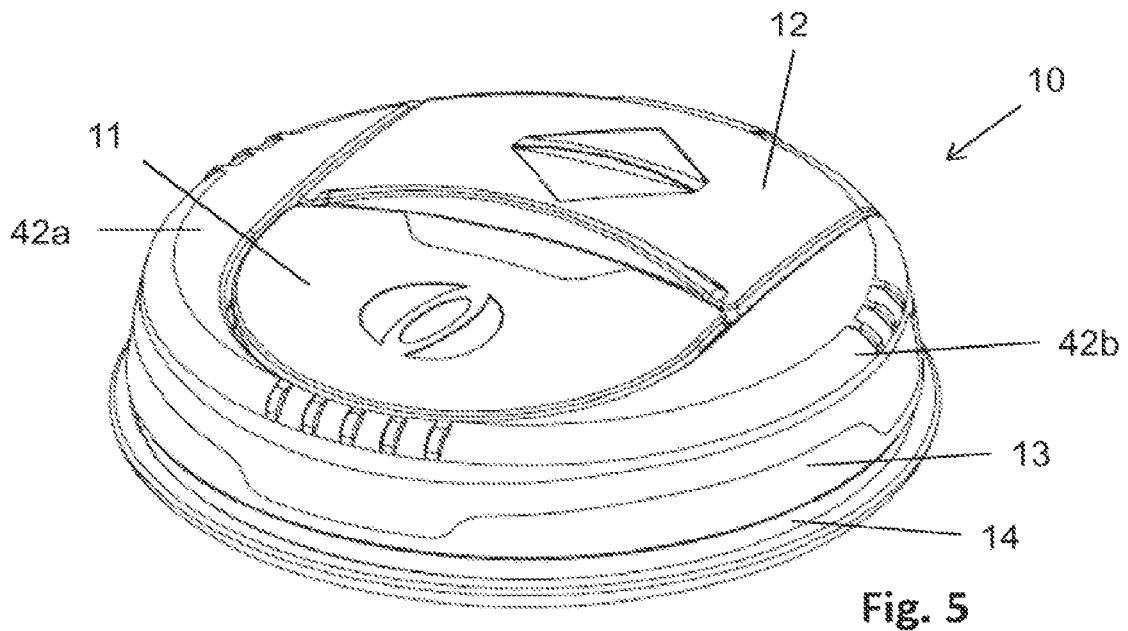
FIG. 5 is a perspective view of a closed lid.
Figure 6:
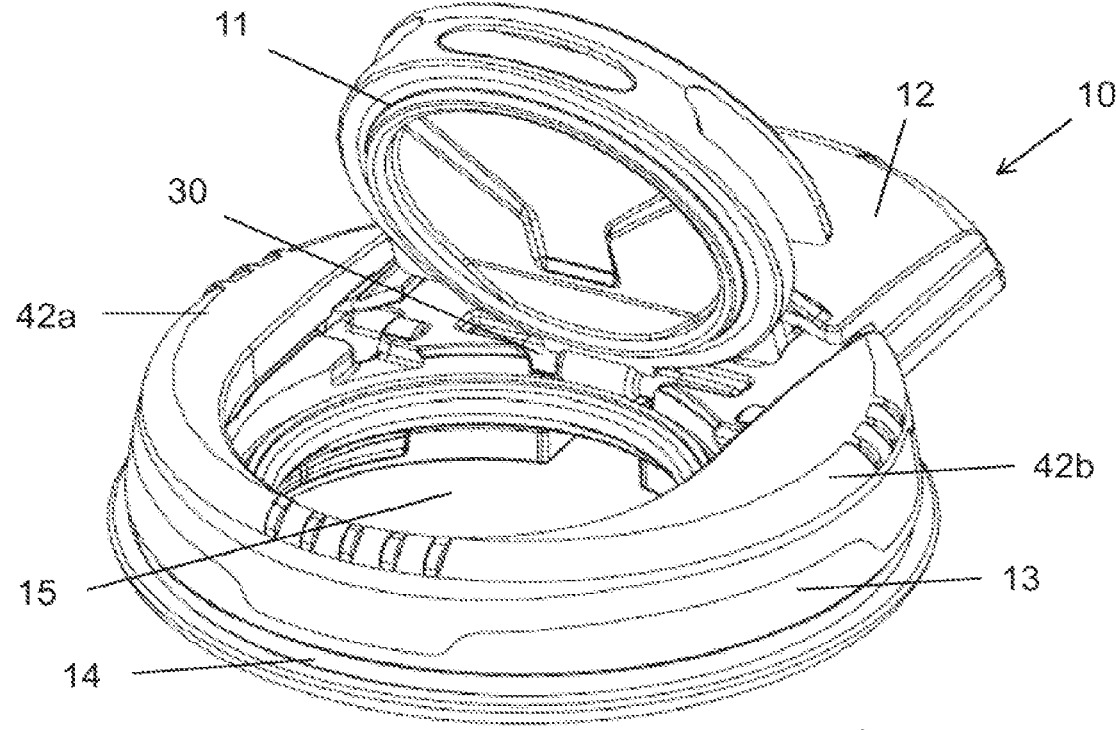
FIG. 6 is a perspective view of an open lid.

FIG. 5 shows the lid 10 with the hatch 11 in a closed configuration. FIG. 6 shows the lid 10 with the hatch 11 in an open configuration.

The lid 10 is made of three main components: the hatch 11, a slider 12 and a base 13. Sliding the slider 12 along a first path allows the lid 10 to be attached to/removed from an implant. Sliding the slider 12 along a second path opens/closes the hatch 11. These processes will be described in more detail below.

The lid 10 has a first side 42a and a second side 42b, the first and second sides 42a, 42b being on opposite sides of the first and second sliding paths of the slider 12.

Figures 19, 20:
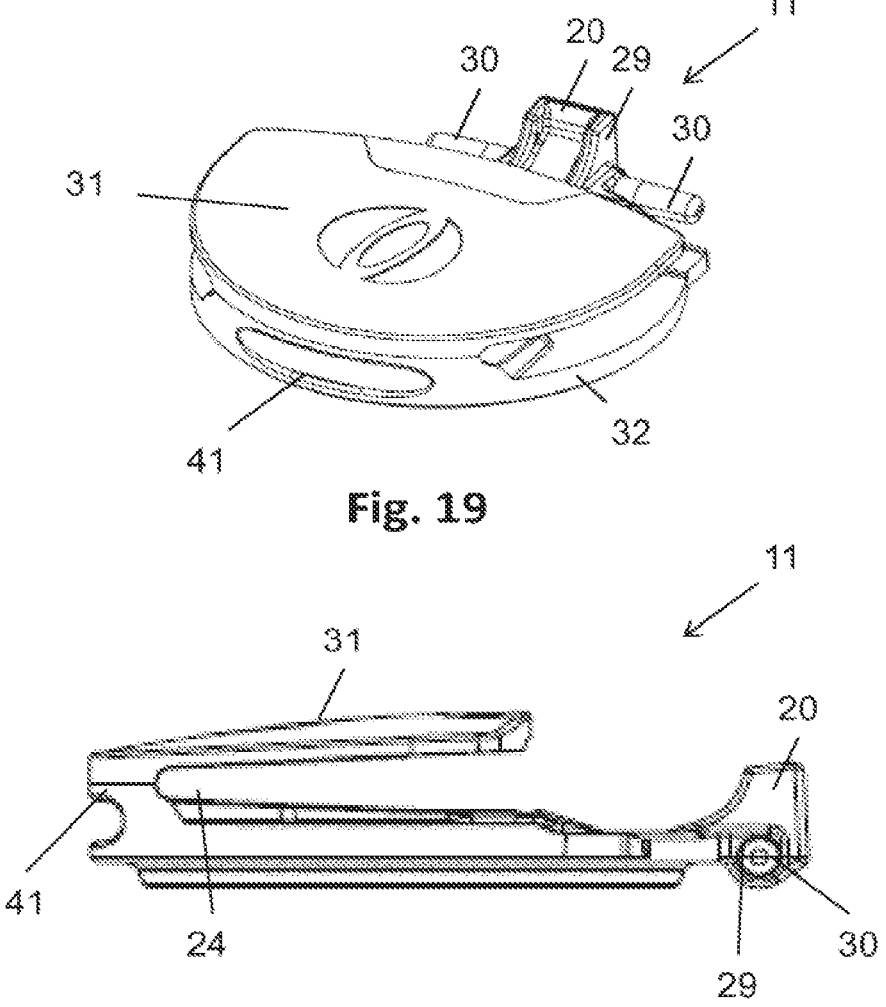
FIG. 19 is a perspective view of a hatch.
FIG. 20 is a side view of a hatch.

The hatch 11 is illustrated in FIGS. 19 and 20. The hatch 11 has a pivoting end 29 and an opening end 41. The pivoting end 29 is arranged to pivot within the lid 10, causing the opening end 41 to open upwardly from the rest of the lid 10 in an arc about the pivoting end 29. The hatch 11 is formed of a top part 31 and a bottom part 32, which are joined together at the opening end 41, with a recess 24 provided between the top part 31 and the bottom part 32. At the pivoting end 29 of the bottom part 32 there is an axel 30 and a projection 20. When the hatch 11 is closed, the projection 20 projects upwardly. When the hatch 11 is open the projection 20 projects more radially outwardly from the lid 10 (but still slightly upwardly). The axel 30 extends horizontally and defines the axis about which the hatch 11 opens.

The slider 12 is illustrated in FIGS. 16, 17 and 18. The slider 12 has a top part 33 and a tongue 19 which projects radially inwardly, away from a radial edge 34 of the slider, from underneath the top part 33. The tongue 19 has at or near its radially inner (or projecting) end an engagement part (e.g. a hook) 28. A gripping part 40 is provided on an upper surface of the top part 33. The gripping part 40 comprises raised and/or lowered parts to assist a user in gripping and sliding the slider 12. Two ridges 21 are provided along opposite edges of the slider 12. The ridges 21 extend in a sliding direction in parallel with the tongue 19. Each ridge 21 has, at its radially inward end, a hook 26. On a lower surface of the top part 33 at its radial edge 34 end is provided a pair of angled members 17. The angled members 17 extend from the radial edge 34 of the slider 12 radially inwardly and towards each other.

Figure 13:
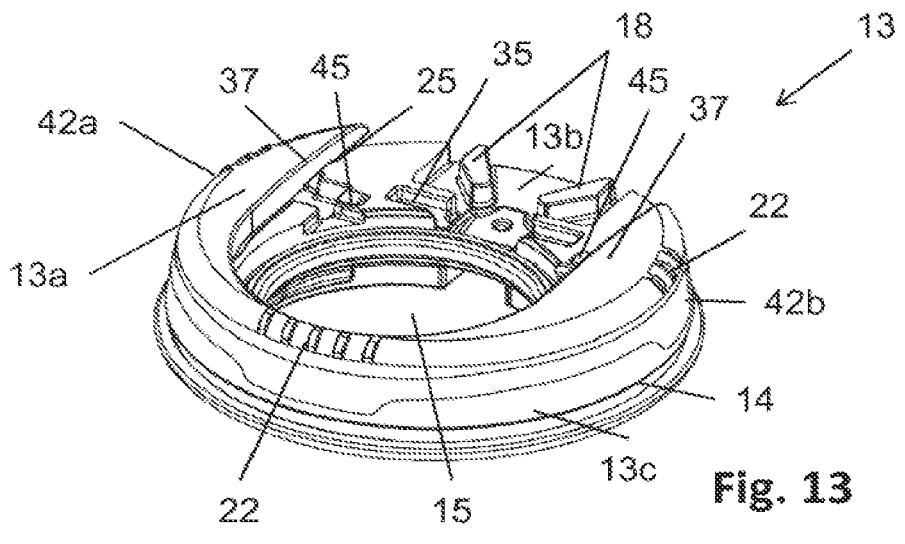
FIG. 13 is a perspective view of a base.
Figure 14:
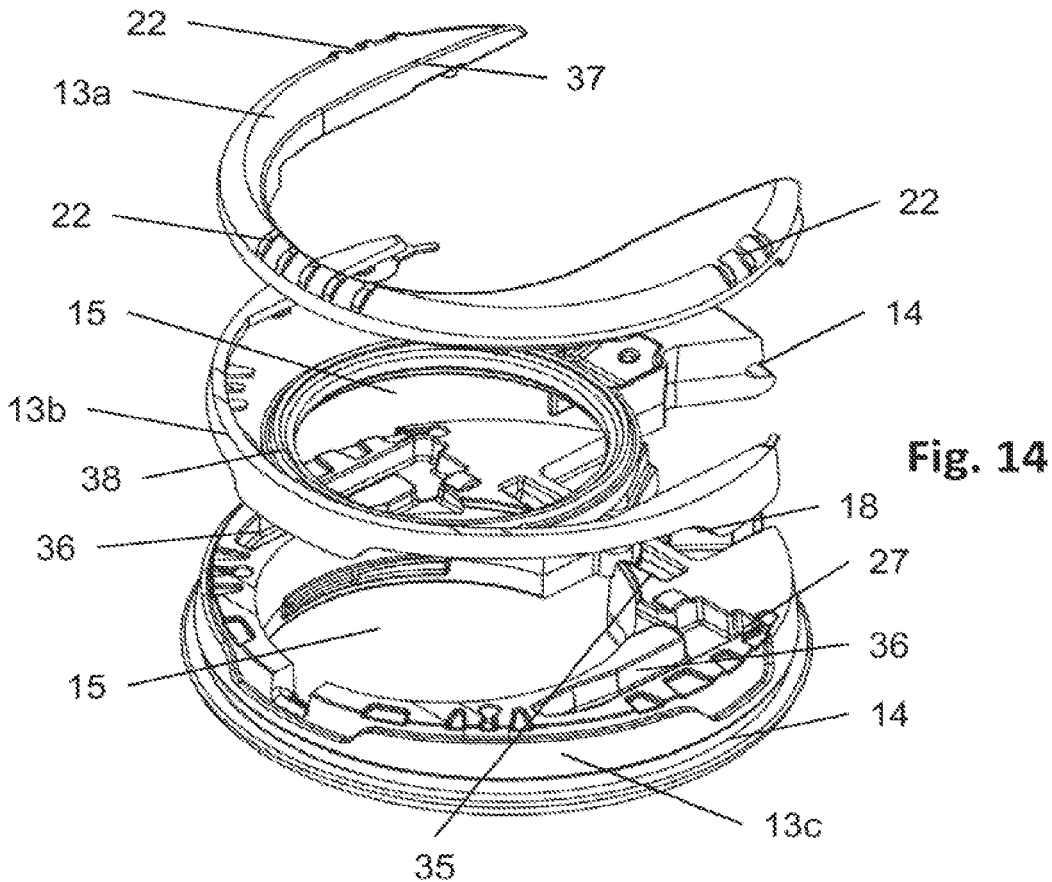
FIG. 14 is an exploded perspective view of components forming a base.
Figure 15:
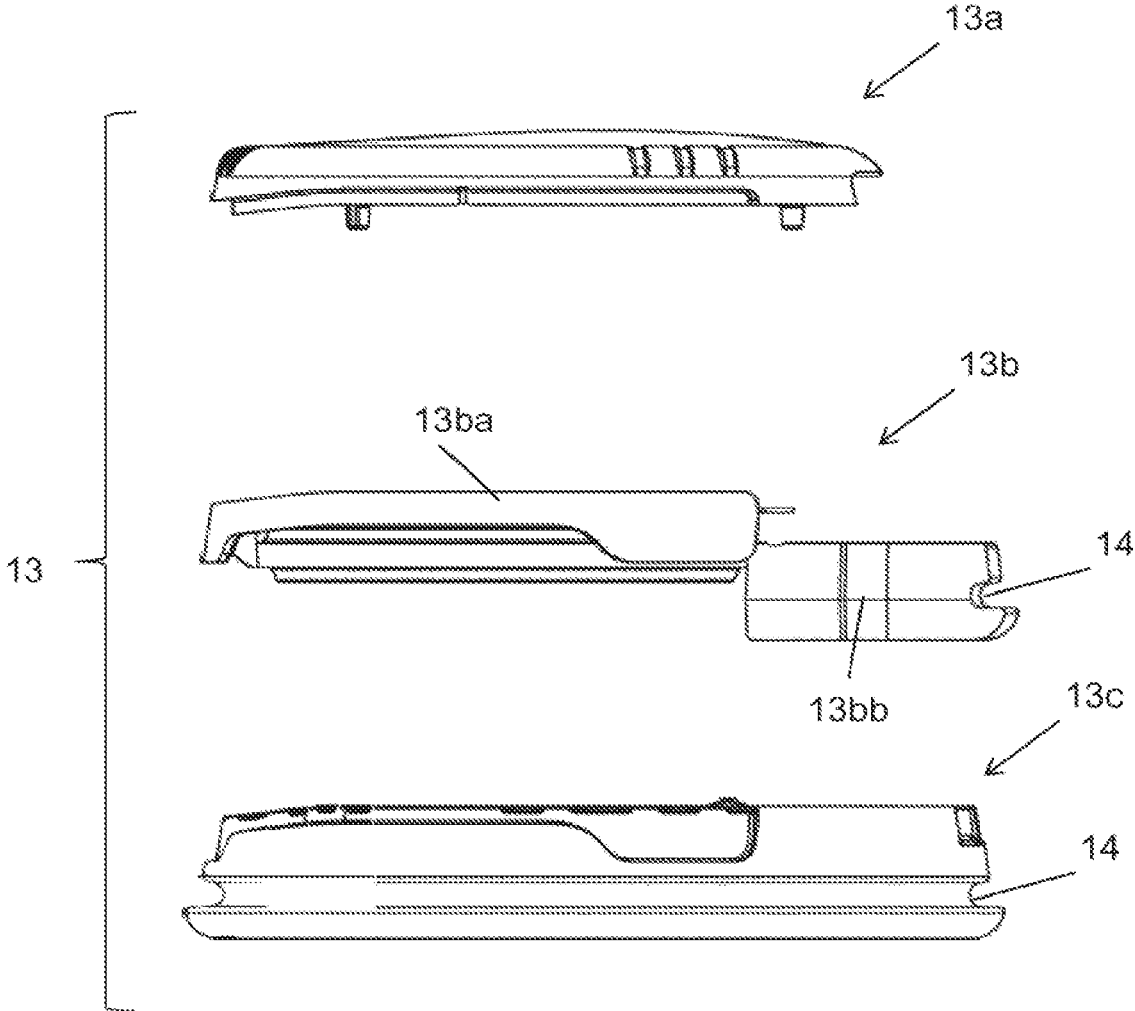
FIG. 15 is an exploded side view of components forming a base.

An embodiment of the base 13 is illustrated in FIGS. 13, 14 and 15. The base is formed of three parts: an upper part 13a, a middle part 13b and a lower part 13c. The upper and lower parts 13a and 13c are formed from a relatively rigid (but still slightly flexible) plastic whereas the middle part 13b is formed from a soft and more flexible plastic or rubber material.

The upper part 13a forms a "C" shape around a circular opening 15. Gripping parts 22 (e.g. grooves and/or ridges or other raised/lowered parts) are provided on the upper surface of the upper part 13a around its edge. The upper part 13a has two opposing radially inner projecting parts 37 which form the upper surfaces of grooves 25 through which the ridges 21 of the slider 12 can slide. The lower surfaces of the grooves 25 are formed from the lower part 13c.

The middle part 13b is formed of an upper middle part 13ba and a lower middle part 13bb. The upper middle part 13ba is located between the upper and lower parts 13a and 13c. The lower middle part 13bb is located beneath the upper part 13a and partly fills a circumferential gap 39 in the lower part 13c (described below). The middle part 13b is formed of a soft, flexible and slightly stretchy plastic or rubber material. A circular opening 15 is formed in the upper middle part 13ba which is delimited by an inner circular edge part 38 of the middle part 13b.

Figures 7, 8:
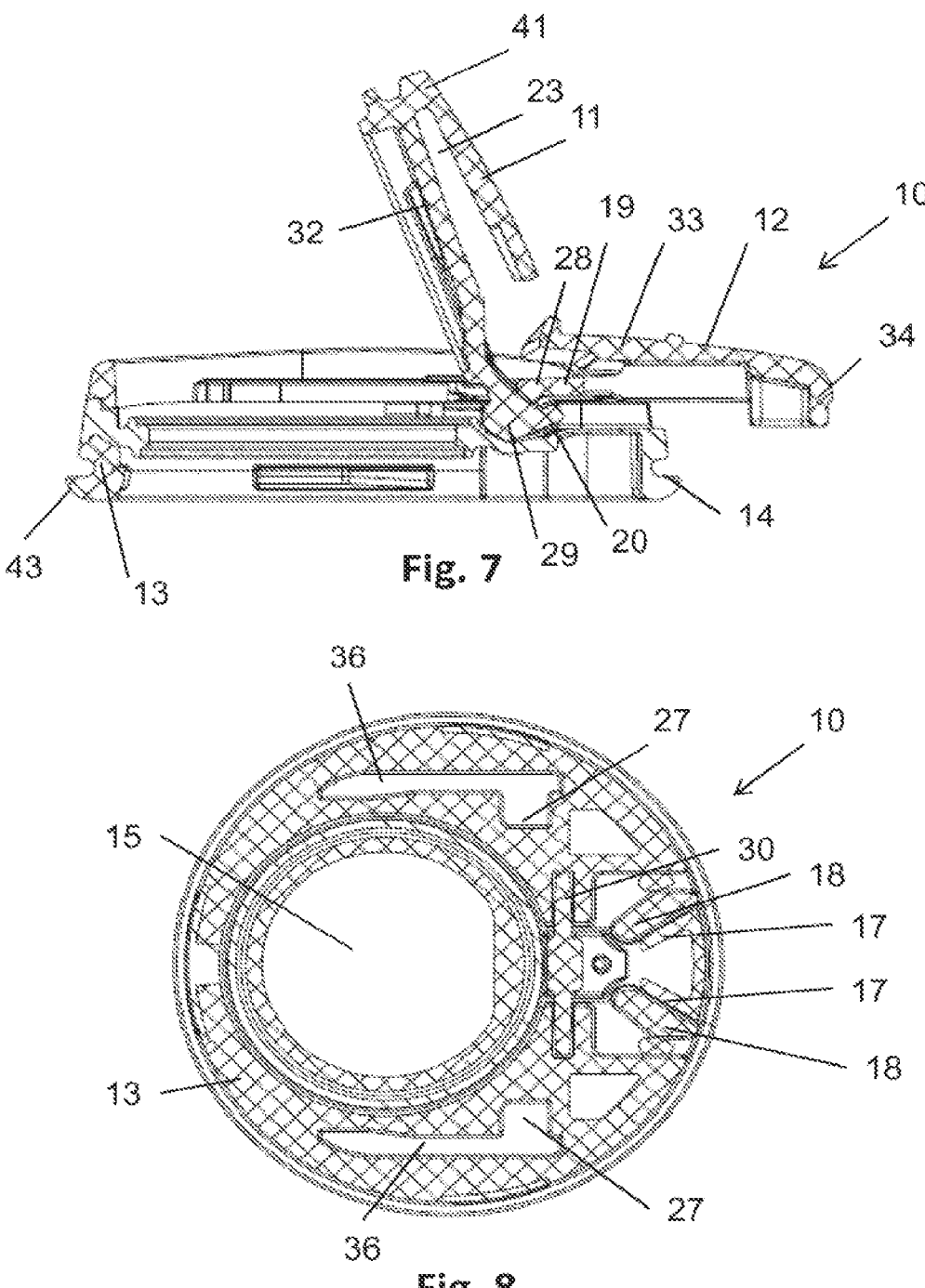
FIG. 7 is a cross-sectional side view of an open lid.
FIG. 8 is a cross-sectional top view of a closed lid.

The bottom part 13c has a generally ring-like shape but with a gap 39 in it breaking its circumference. The gap 39 can be seen in FIG. 11, for example. The opening 15 continues through the bottom part 13c. The bottom part 13c contains a pair of grooves 36 which are located beneath the projecting parts 37 of the upper part 13a, thereby forming the grooves 25 through which the ridges 21 of the slider 12 can slide. Recesses 27 (as shown in FIG. 8) are located at ends of each groove 36 to help hold the hatch 11 open (this is described in more detail below). A further groove 35 is provided on either side of (across) the gap 39 for the axel 30 of the hatch 11 to rest and rotate in. A pair of angled members 18 is provided on the bottom part 13c on either side of the gap 39. These angled members 18 of the bottom part 13c. The angled members 18 are located and positioned such that the angled members 17 of the slider 12 abut against them when the slider 12 is in a closed configuration, as can be seen in FIG. 8.

When the upper, middle and lower parts 13a-c of the base 13 are assembled, the opening 15 is delimited by the soft flexible edge part 38 of the middle part 13b and it is the edge part 38 which sits in and engages with the groove 6 on the implant 1 when the lid 10 is connected to the implant 1.

A groove 14 is provided around the exterior circumference of the base 13 in its lower part 13c and lower middle part 13bb. This groove 14 allows other devices (such as connectors, evacuation sleeves, bags, catheters etc.) to be connected to the lid 10, e.g. while it is attached to the implant 1. A projection 43 is provided around the lid 10 on the lower side of the groove 14. This projection 43 can help to prevent any device connected to the groove 14 from sliding down the lid 10. The hatch 11 can be opened and closed while such other devices are connected to the lid 10 to allow evacuation of waste from the patient.

Figure 33:
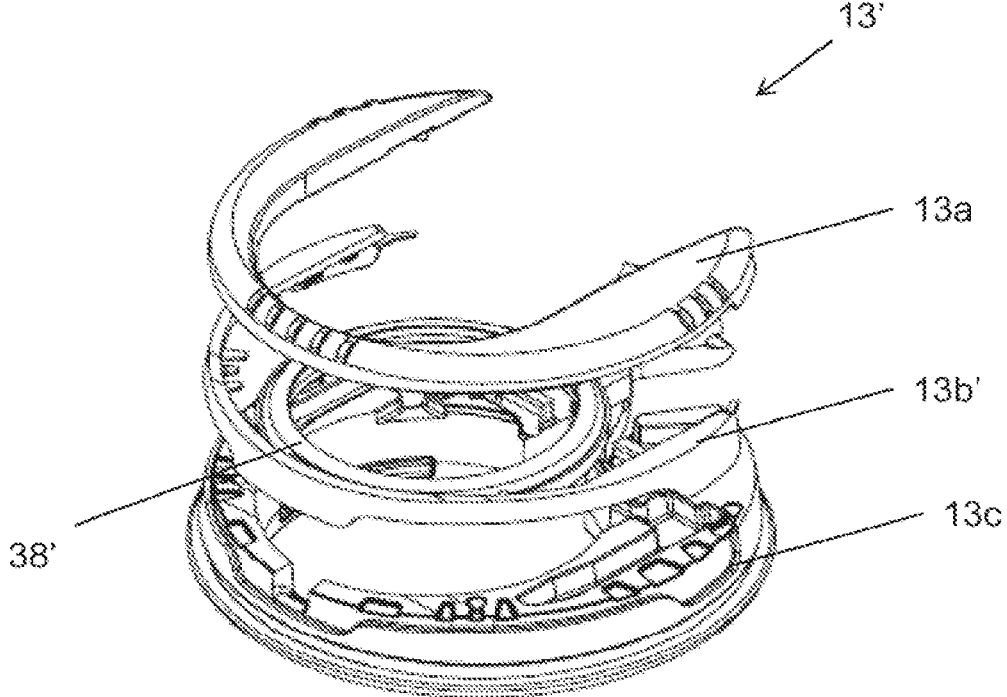
FIG. 33 is an exploded perspective view of components forming an alternative embodiment of the base.
Figure 34:
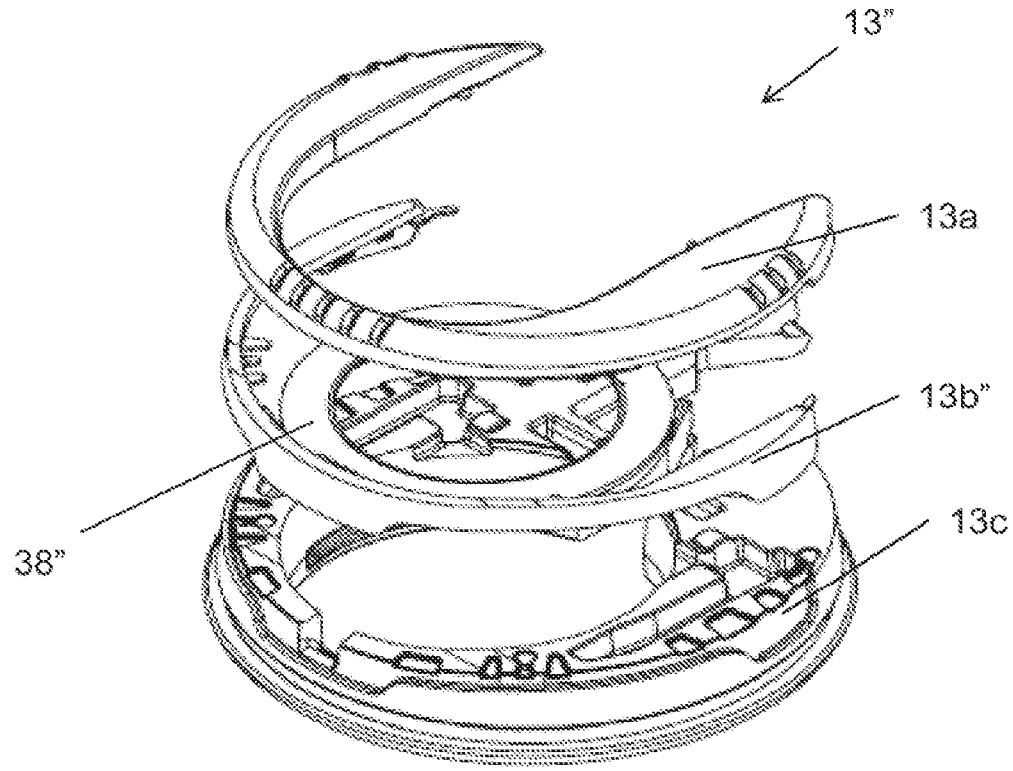
FIG. 34 is an exploded perspective view of components forming a further alternative embodiment of the base.

FIGS. 33 and 34 show alternative embodiments of the base 13' and 13". In these bases 13' and 13", the upper and bottom parts 13a and 13c are the same as those in base 13. However, the middle parts 13b' and 13h" are slightly different. Specifically, the shapes of their respective edge parts 38' and 38", delimiting the opening 15, are slightly different to that of the edge 38 of middle part 13b.

The operation of the lid 10 will now be described.

There are two main operations of the lid 10:

(i) attaching/detaching the lid 10 to/from an implant 1; and (ii) opening/closing the hatch 11 of the lid 10 (whilst attached to an implant 1).

First, the attaching/detaching of the lid 10 to/from an implant 1 will be described.

Figure 12:
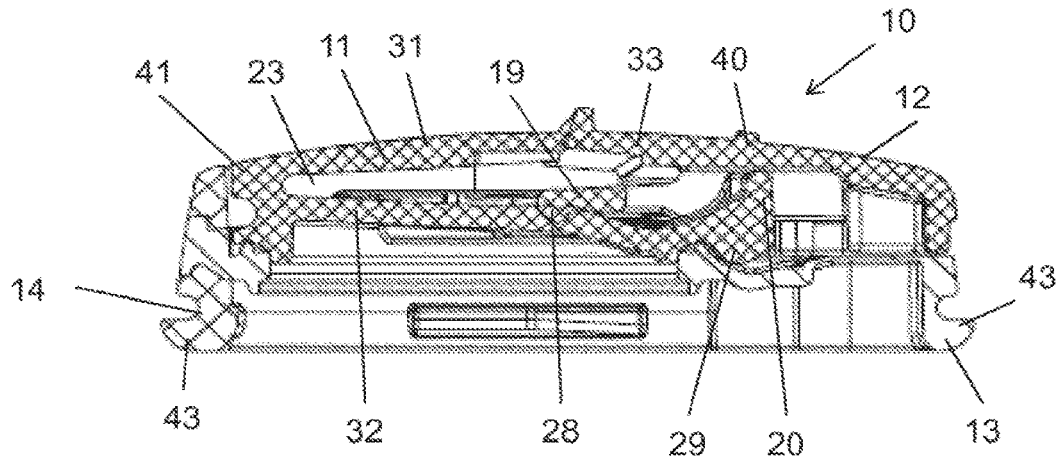
FIG. 12 is a cross-sectional side view of a closed lid.

In order to attach the lid 10 to an implant 1, the lid 10 must start in the closed relaxed configuration illustrated in FIG. 12. A user must then squeeze the lid 10 by pushing down the hatch 11 and, at the same time, pushing the radial edge 34 of the slider 12 radially inwardly, such that the ridges 21 move through/along the grooves 25. This causes the top part 33 of the slider 12 to move over the top part 31 of the hatch 11. The top part 31 of the hatch 11 then extends partly between the top part 33 and tongue 19 of the slider 12.

Figure 9:
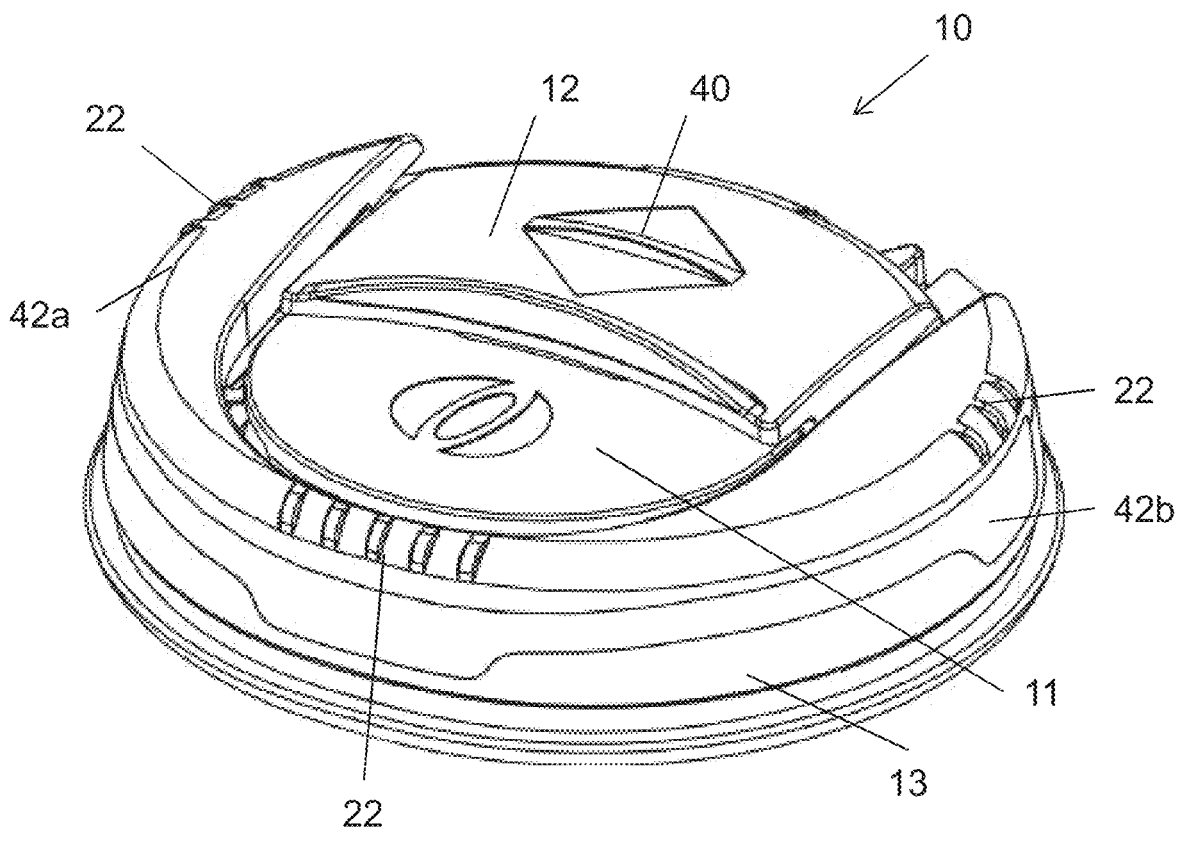
FIG. 9 is a perspective view of a lid in a stressed configuration ready for placing on an implant.
Figure 10:
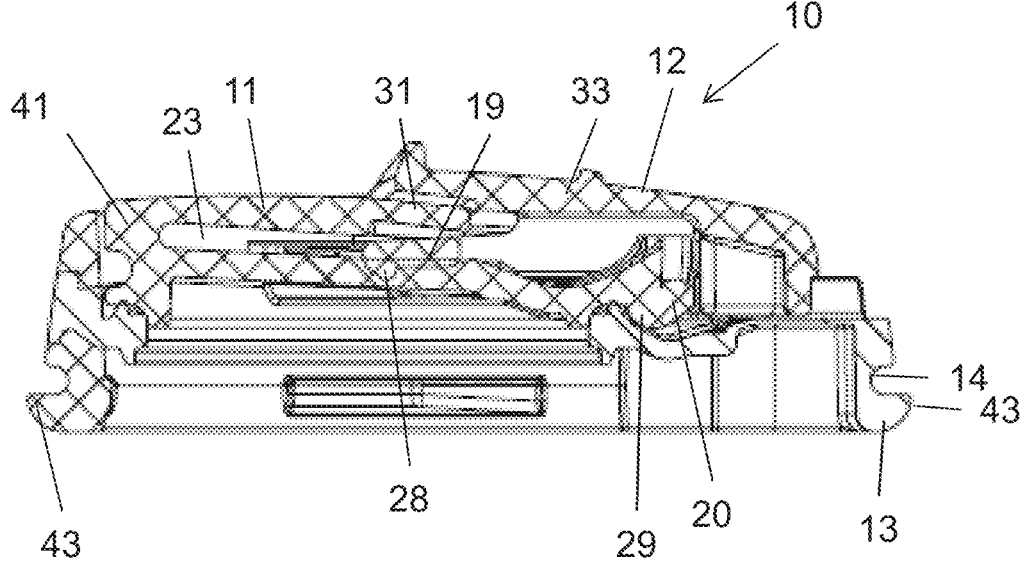
FIG. 10 is a cross-sectional side view of a lid in a stressed configuration ready for placing on an implant.

The recess 23 between the top part 31 and bottom part 32 of the hatch 11 allows the top part 31 to be pressed downwards in this way. This is illustrated in FIGS. 9 and 10, which show a "stressed" configuration of the lid 10. It can be seen that the recess 23 is smaller in FIG. 10 (in the stressed configuration) than in FIG. 12 (in the closed relaxed configuration).

Figure 11:
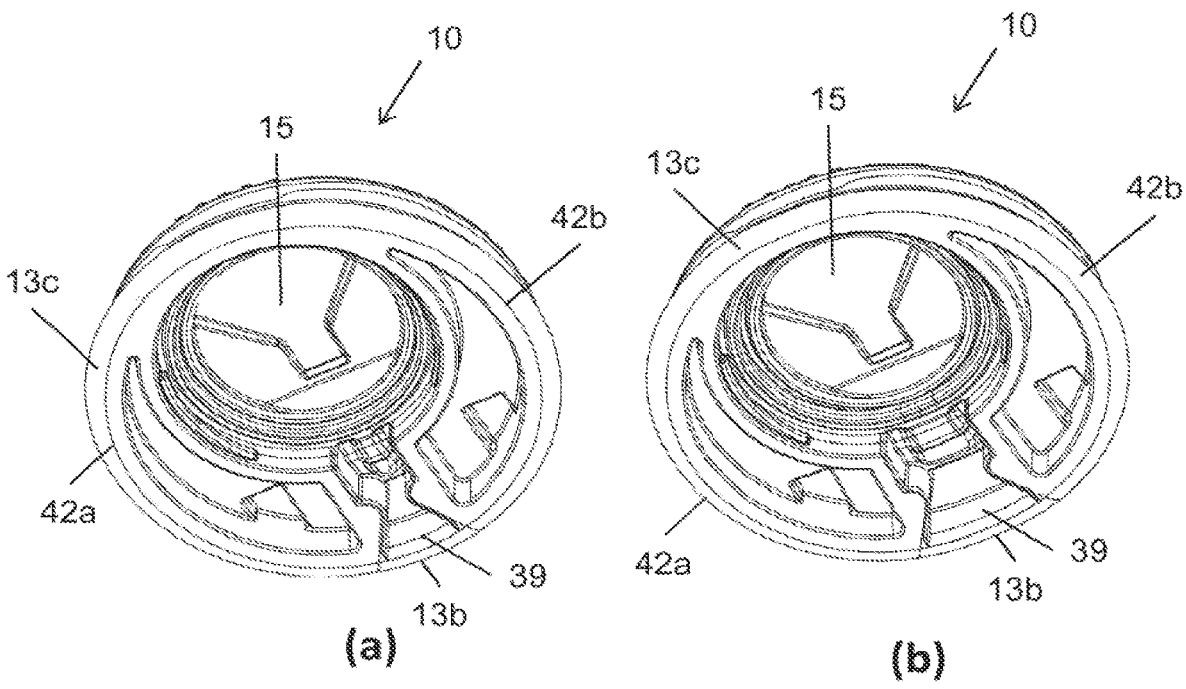
FIGS. 11(a) and (b) are perspective views of a closed lid from beneath in (a) a relaxed configuration and (b) a stressed configuration.

By pushing the slider 12 radially inwards in this way, this causes the angled parts 17 of the slider 12 to push against the angled parts 18 of the base 13. This pushes the angled parts 18 of the base 13 apart, increasing the distance between the opposing halves of the top and bottom parts 13*a* and 13*c*, stretching the middle part 13*b*, and thereby increasing the size of the opening 15. This is illustrated in FIGS. 11(*a*) and (*b*), which show how the size of the gap 39 in the bottom part 13*c* of the base 13, is larger in the stressed configuration (b) than in the relaxed configuration (a).

Increasing the size of the opening 15 in this way allows the user to then place the lid 10 over the end of the implant 1.

The user then relaxes their grip on the lid 10 such that they are no longer squeezing the slider 12 radially inwardly. This causes the slider 12 to move back towards (but not fully into) the relaxed configuration of FIG. 12.

The user then squeezes the lid 10 at its first and second sides 42*a* and 42*b* (e.g. with the gripping parts 22), perpendicularly to the sliding motion of the slider 12, which causes the slider 12 to move back fully into the relaxed configuration of FIG. 12. At this point, the opening 15 returns to its normal or relaxed size, whereby the edge part 38 of the middle part 13*b* of the base 13 is positioned in the groove 6 on the exterior part 4 of the implant 1. A "click" sound may be heard at this point, indicating to the user that the lid 10 is properly attached onto the implant 1. The lid 10 is then attached to and located on the implant 1.

As the middle part 13*b*, in particular its edge part 38, is made from a flexible and soft material, this creates a seal with the implant 1 and the lid 10 is therefore in sealing engagement with the implant 1.

In order to remove the lid 10 from the implant 1, the same steps are performed in reverse. The lid 10 is squeezed by pushing the radial edge 34 of the slider 12 radially inwardly to increase the size of the opening 15. The lid 10 can then be removed from the implant 1. The user then relaxes their grip on the lid 10 such that they are no longer squeezing the slider 12 radially inwardly, thereby causing the lid 10 to return to its normal or relaxed configuration.

The opening/closing of the hatch 11 of the lid 10 will now be described. This is performed when the lid 10 is attached to an implant 1 to allow the evacuation of waste from the ileum.

As described above, two ridges 21 are provided on opposite sides of the slider 12. The ridges 21 can slide along/within the pair of grooves 25 which are provided in the base 13 of the lid 10. A hooking part 26 is provided at the end of each ridge 21.

In order to open the hatch 11, the slider 12 is slid radially outwardly from the rest of the lid 10 such that the ridges 21 move along through the grooves 25. This process is described in more detail with reference to FIGS. 7 and 12. FIG. 7 is a cross-sectional side view of the lid 10 with the hatch 11 in an open configuration and FIG. 12 is a cross-sectional side view of the lid 10 with the hatch 11 in a closed configuration.

When the slider 12 is slid radially outwardly from the rest of the lid 10, the engagement part 28 (e.g. a hook) on the tongue 19 slides along to and engages with the projection 20 on the hatch 11, pressing on the projection 20 and thereby causing the hatch 11 to pivot about the axel 30 at its pivoting end 29 and open upwardly.

When the slider 12 is slid out and the hatch 11 is open, the hooks 26 on the end of each ridge 21 of the slider 12 are located in the recesses 27 in the base 13.

In this state, the hatch 11 is held open because the shape and material (plastic) of the tongue 19, combined with the shape of the base 13, cause the tongue 19 to function like a spring, exerting a spring force on the hatch 11. If a user tries to close the hatch 11 with a force (or a force accidentally presses on the hatch 11), while the slider 12 is slid out from the rest of the lid 10, the hatch 11 will close but it will spring back open again when the force is removed due to the spring force of the tongue 19 acting on the hatch 11.

In order to close the hatch 11, the slider 12 is pushed radially inwardly. This causes the spring force of the tongue 19 acting on the hatch 11 to stop, as the engagement part 28 of the tongue 19 is slid away from the projection 20 and over the bottom part 32 of the hatch 11, thereby pressing down on the bottom part 32 of the hatch 11 and causing it to close.

The slider 12 has two "spring" bumps 44 (see FIG. 18) on its lower side and on either side of the tongue 19. The spring bumps 44 slide over two corresponding bumps 45 located on either side inside the base 13 (see FIG. 13). The slider 12 is held in a closed position by its spring bumps 44 being held in place (prevented from sliding) by the bumps 45 on each side of the base 13. The slider 12 has to be pushed with sufficient force that its spring bumps 44 can overcome the resistance from, and move over, the bumps 45 in the base 13.

When the slider 12 is in the closed position, the tongue 19 presses downwards on the bottom part 32 of the hatch 11, thereby pressing the hatch 11 down against the base 13, specifically, its middle part 13*b*, whereby the hatch 11 is closed in sealing engagement with the base 13.

The lid 10 is made of plastics materials. The slider 12 is made of POM: Medical grade copolymer granules of Poly-OxyMethylene.

The hatch 11 is made of PBT: Medical grade copolymer granules of PolyButyleneTerephthalate (polyester).

The top and bottom parts 13*a* and 13*c* of the base 13 are made of PP (polypropylene). In an alternative embodiment, the top and bottom parts 13*a* and 13*c* of the base 13 are made of ABS: Medical grade copolymer granules of AcrylonitrileButadieneStyrene. The middle part 13*b* of the base 13 is made of Mediprene®: Medical grade elastomer granules of StyreneEthyleneButyleneStyrene.

The slider 12, hatch 11 and top, middle and bottom parts 13*a*-*c* of the base 13 are injection moulded, assembled and packed in a controlled process and environment, which is clean but not (necessarily) sterile.

The base 13 is manufactured by first injection moulding the top and bottom parts 13*a*, 13*c* from PP, in separate first and second tools. These parts 13*a*, 13*c* are then inserted into a third tool, where Mediprene® is injected to both form the middle part 13*b* and join the top and bottom parts 13*a*, 13*c* (via the middle part 13*b*), thereby creating a complete base 13. This process is often referred to as 2K injection moulding.

The lid 10 is reusable but should be replaced on a weekly basis.

In order to clean the lid 10, it is recommended to rinse it in tap water. However, the lid 10 will withstand soap, household detergents and boiling water. It can also be soaked in 70% alcohol. After such cleaning it should always be rinsed carefully afterwards.

A connector can be attached to the lid 10 in, or partly in, the groove 14.

Figure 21:
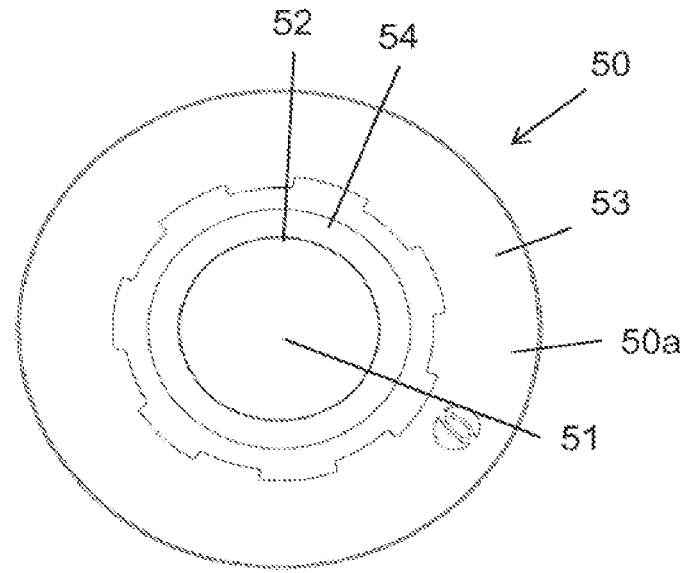
FIG. 21 is a top view of an embodiment of a connector.
Figure 22:
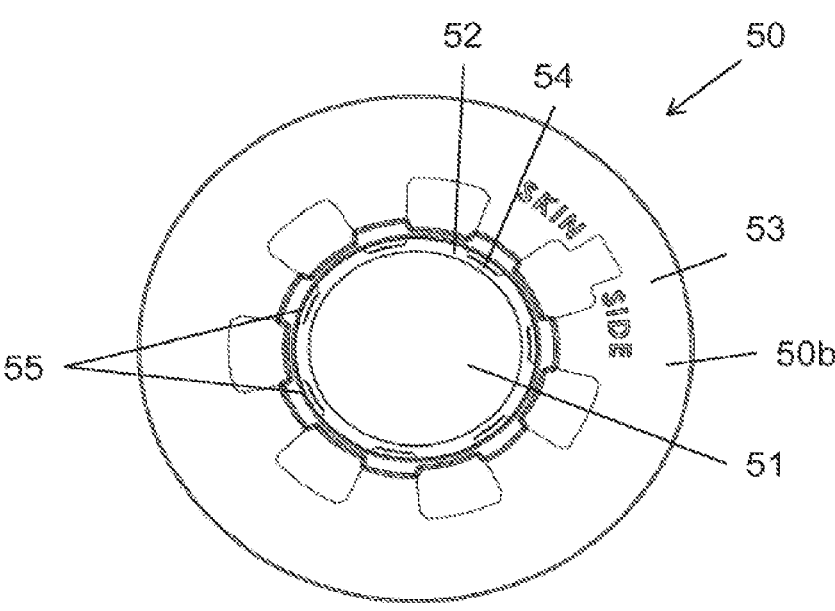
FIG. 22 is a bottom view of the connector of FIG. 21.
Figure 23:
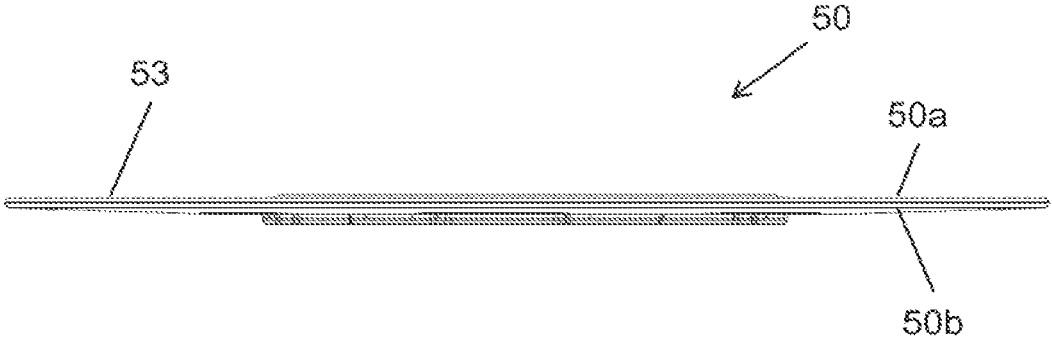
FIG. 23 is a side view of the connector of FIG. 21.
Figure 24:
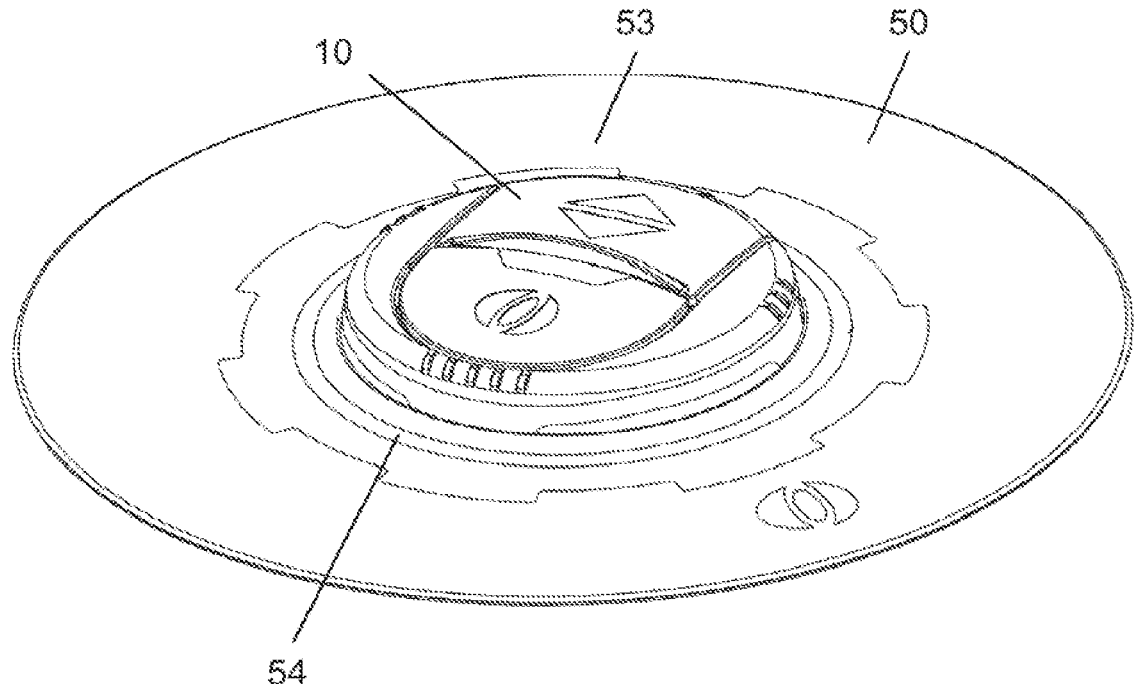
FIG. 24 is a perspective view of a lid with the connector of FIG. 21 attached thereto.

A preferred embodiment of a connector 50 is shown in FIGS. 21 to 23. FIG. 24 shows the connector 50 attached to a lid 10.

The connector 50 provides a flat surface to which further devices such as evacuation sleeves, catheters or bags may be attached (e.g. with adhesive). Alternatively, such further devices may be provided with a connector 50 already attached, for attachment to a lid 10.

The connector 50 is a circular disc with an opening 51 in the middle. The diameter of the opening 51 is sized such that the inner edge 52 of the connector 50 fits around the lid 10 just above the groove 14.

In alternative embodiments, the connector 50 is sized slightly smaller such that its inner edge 52 fits around implant 1 just above the groove 6. The connector 50 may then be attached directly to the implant 1.

The connector 50 has a top side 50*a* and a bottom or skin side 50*b*. The top side 50*a* provides the flat surface to which further devices may be attached (e.g. with adhesive).

The connector 50 is made of two main parts: an outer ring 53 and an inner ring 54.

The outer ring 53 is made of a relatively hard or stiff plastic (e.g. polypropylene) and the inner ring 54 is made of a soft rubbery material such as Mediprene®. Forming the inner ring 54 from a soft material allows it to sealingly engage with the lid 10 (or the implant 1), thereby preventing leaks. Forming the outer ring 53 from a stiffer material allows it to form a rigid base, e.g. to which a further device may be attached, and makes it easier to position and attach the connector 50 to the lid 10 (or implant 1).

The stiff outer ring 53 of the connector 50 has a number of tongues 55 (seven tongues are provided in the embodiment shown). The tongues 55 extend from the rest of the outer ring 53 through the inner ring 54 towards, but not quite as far as, the inner edge 52 of the connector 50. The tongues 55 are provided on the skin side 50*b* of the connector 50.

The inner diameter of the inner tips (ends) of the tongues 55 matches, or nearly matches, the diameter of the groove 14 provided around the lid 10 (i.e. it is slightly smaller than or slightly larger than or the same as the diameter at the bottom of the groove 14, depending on how tight a fit is desired for the connector 50 on the lid 10). The inner diameter of the inner ring 54 is smaller than the inner diameter of the tips (ends) of the tongues 55 and smaller than the outer diameter of the lid 10, thereby creating a snug and sealing fit of the inner ring 54 against the lid 10.

Figure 25:
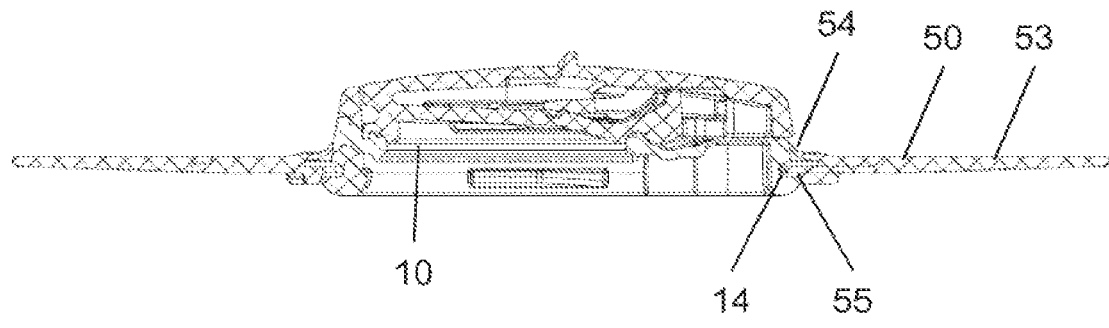
FIG. 25 is a cross-sectional side view of a closed lid with the connector of FIG. 21 attached thereto.
Figure 26:
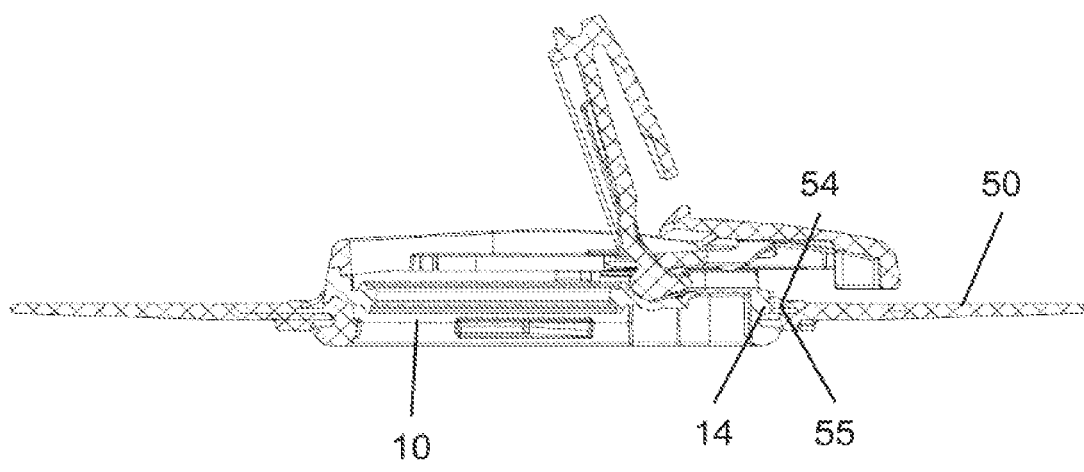
FIG. 26 is a cross-sectional side view of an open lid with the connector of FIG. 21 attached thereto.

The tongues 55 are made of the same stiff material as the rest of the outer ring 53. These tongues 55 will flex slightly and, when the connector 50 is connected to a lid 10 (or implant 1) will click into the groove 14 in the lid 10 (or the groove 6 in the implant 1) thereby fixing the connector 50 to the lid 10 (or implant 1), as shown in FIGS. 25 and 26.

The soft rubbery inner ring 54 forms a very thin, smooth inner circle, whose inner diameter is slightly smaller than the outer diameter of the lid 10 just above the groove 14. This means that the inner ring 54 can seal tightly against the lid 10 just above the groove 14, as shown in FIGS. 25 and 26.

Thus, the tongues 55 engage with the lid 10 in the groove 14, and the inner ring 54 seals with the lid 10 just above the groove 14. Together, the tongues 55 and the inner ring 54 function to connect and seal the connector 50 to the lid 10. However, this only works correctly if the connector 50 is placed with the correct side facing upwards, i.e. with the tongues 55 on the lower (or skin) side 50*b*.

In an alternative embodiment, the two sides of the connector are the same and so it can be used either way up.

As described above, the projection 43 around the lid 10 at the lower side of the groove 14 helps to prevent the connector 50, when connected to the lid 10, from being pushed down the lid 10, e.g. to between the lid 10 and the patient's skin.

The connector 50 is manufactured using injection moulding. First, the outer ring 53 (with its tongues 55) is formed by injection moulding it in a first tool. The outer ring 53 (with its tongues 55) is then placed in a second tool and the inner ring 54 is injection moulded onto the outer ring 53 in the second tool, thereby joining the two ring parts 53, 54 together.

Alternative connectors are shown in FIGS. 27 to 32.

Figure 27:
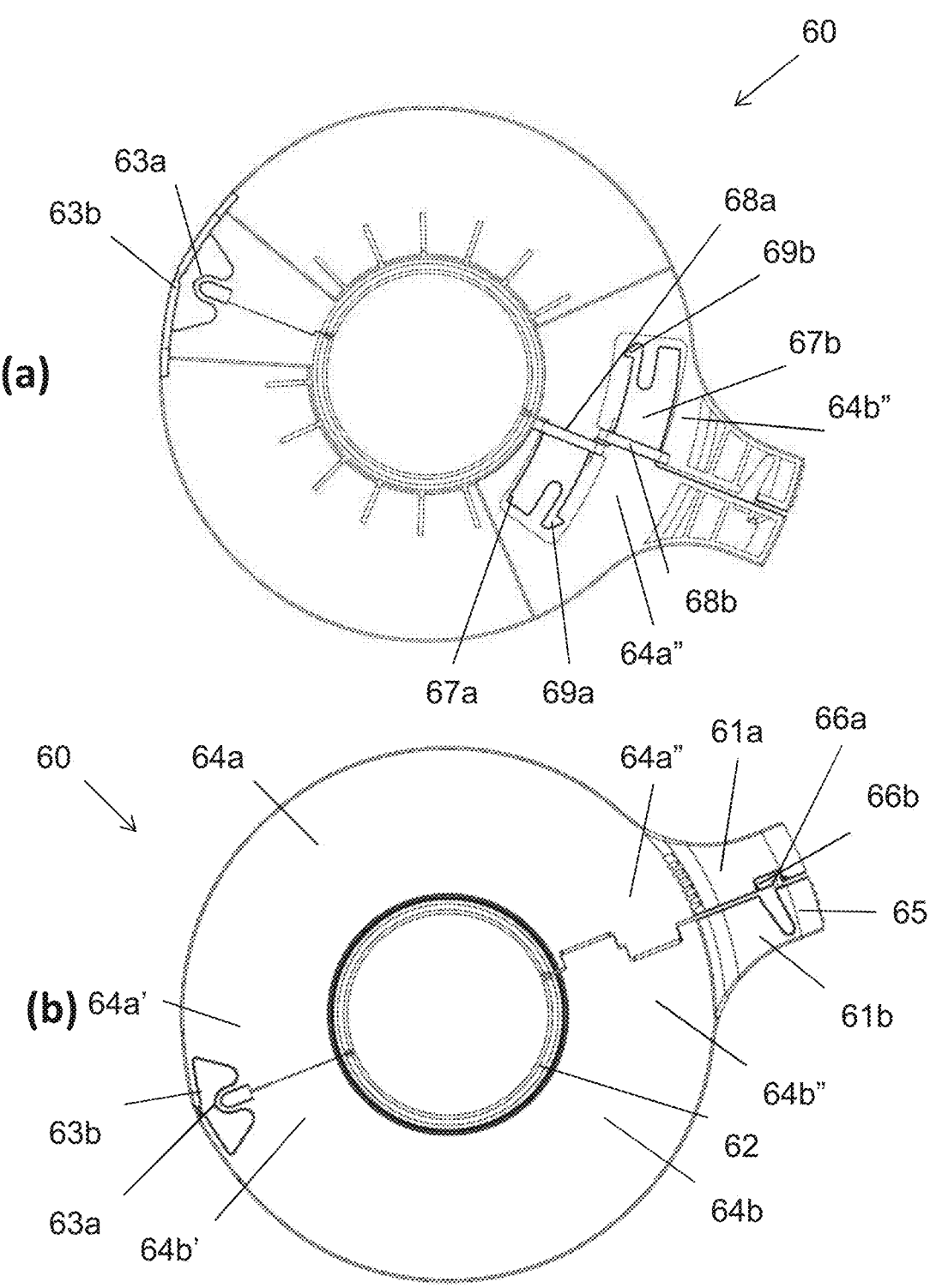
FIG. 27 shows (a) bottom and (b) top views of an embodiment of a connector in a closed configuration.
Figure 28:
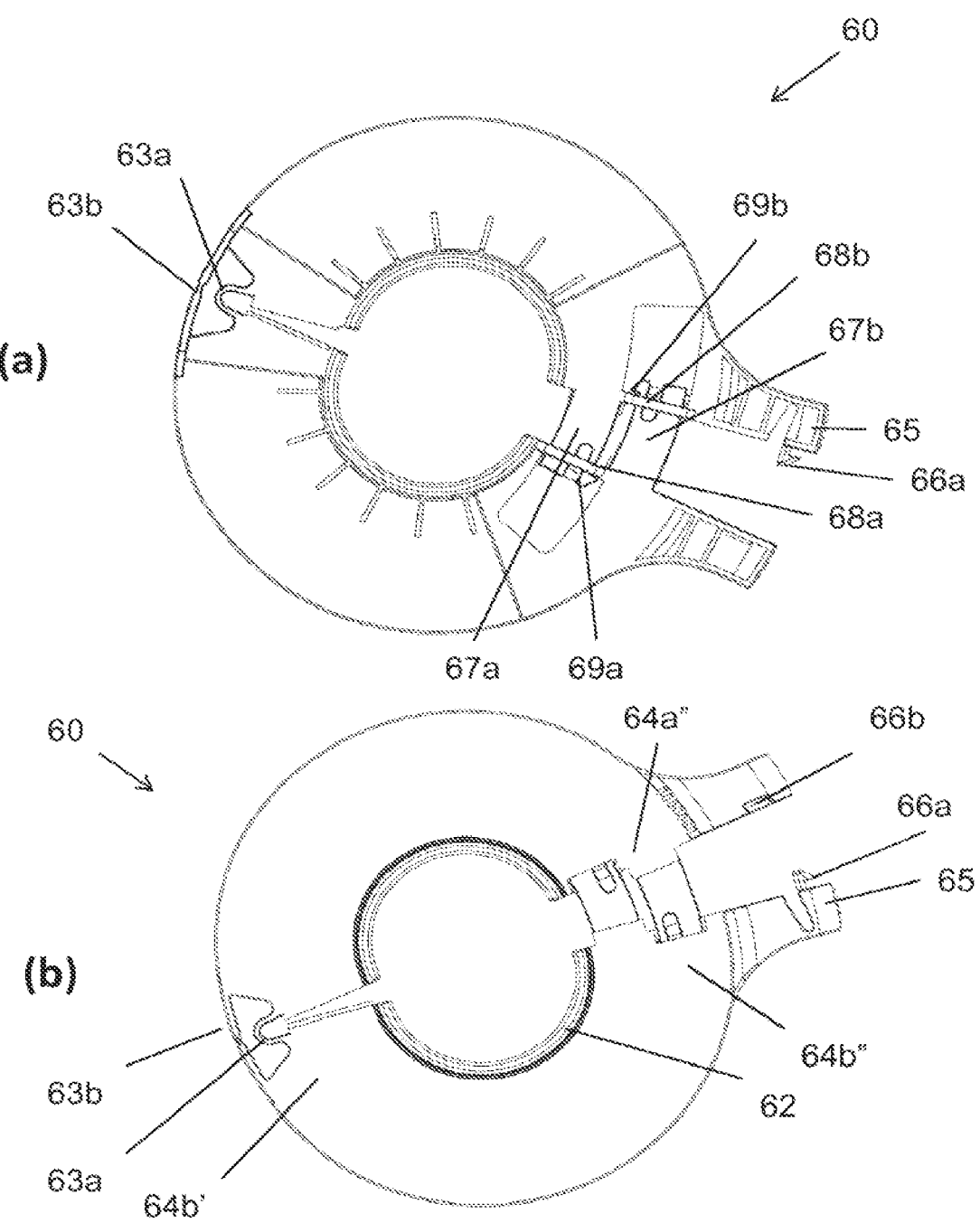
FIG. 28 shows (a) bottom and (b) top views of the connector of FIG. 27 in an open configuration.

FIGS. 27 and 28 show a connector 60 in closed and open configurations, respectively. The connector 60 is substantially ring-shaped and is formed of two relatively planar halves 64*a* and 64*b*. Each half 64*a*, 64*b*, has a joined end 64*a*', 64*b*' and a connecting end 64*a*" and 64*b*".

A device such as a sleeve, catheter or bag may be adhered to the upper surface of these halves 64*a* 64*b*.

A connecting edge 62 is provided around an inner circumference of the two halves 64*a* 64*b*. The connecting edge 62 is formed of a soft rubbery material and is sized and dimensioned so as to fit in and seal with the groove 14 in the lid (or in the groove 6 in an implant 1).

The two halves 64*a*, 64*b* are joined at their joined ends 64*a*', 64*b*' by a pair of relatively thin and flexible bending member 63*a*, 63*b*.

At the connecting ends 64*a*", 64*b*", radially outwardly projecting gripping parts 61*a* and 61*b* are provided, which can be connected together (thereby closing the con-nector 60) by means of a hook 66*b* provided on the second gripping part 61*b* and a hooking member 66*a* provided on the first gripping part 61*a*, around which the hook 66*b* can hook when a compression part 65 provided on the second gripping part 61*b* is compressed and then released.

A pair of opening arms 67*a* and 67*b* are also provided at the connecting ends 64*a*" and 64*b*" of the halves 64*a*, 64*b*. Specifically, an opening arm 67*b* is provided at the connecting end 64*a*", which passes under a retaining mem-ber 68*b* provided on the other connecting end 64*b*". Similarly, an opening arm 67*a* is provided at the connecting end 64*b*", which passes under a retaining member 68*a* provided on the other connecting end 64*a*". Hooks 69*a* and 69*b* are provided at the end of each opening arm 67*a*, 67*b* which, when the connector 60 is opened to its fullest extent, hook against the retaining members 68*a* and 68*b*, thereby pre-venting the connector 60 from being opened too far.

The same soft rubbery material that is provided along the connecting edge 62 is also provided along the joining edges of the connector 60 at the joined ends 64*a*', 64*b*' and connecting ends 64*a*", 64*b*" so that, when the connector 60 is closed, the two halves 64*a*, 64*b* are in sealing connection with each other.

The connector 60 is provided in a closed state as illustrated in FIG. 27. In order to attach the connector 60 to a lid 10, the connector 60 is opened by pressing on the compression part 65 to release the hook 66*b* from the hooking member 66*a*. The two halves 64*a*, 64*b* of the connector 60 can then be opened. The connector 60 is then placed around the groove 14 in the lid 10 (or around the groove 6 in an implant 1) and the two halves 64*a*, 64*b* of the connector 60 are then moved back together so that the hook 66*b* hooks onto the hooking member 66*a* again and the connecting edge

62 is located in the groove 14 in the lid (on in the groove 6 in an implant 1), thereby holding the connector 60 in place.

In order to remove the connector 60 from a lid 10 or implant 1, the same procedure is performed again except that the connector 60 is removed from the lid 10 or implant 1, rather than being placed around it.

The connector 60 is manufactured by injection moulding. The two halves 64a, 64b of the connector 60 are injection moulded together in a first tool. Then they are placed in a second tool and the soft rubbery material is injection moulded on to them along the connecting edge 62 and joining edges between the two halves 64a, 64b.

The two halves 64a, 64b of the connector 60 are then connected together at their connecting ends 64a", 64b" by inserting the opening arms 67a and 67b under their respective retaining members 68a, 68b, so that the connector 60 is ready for use.

Figure 29:
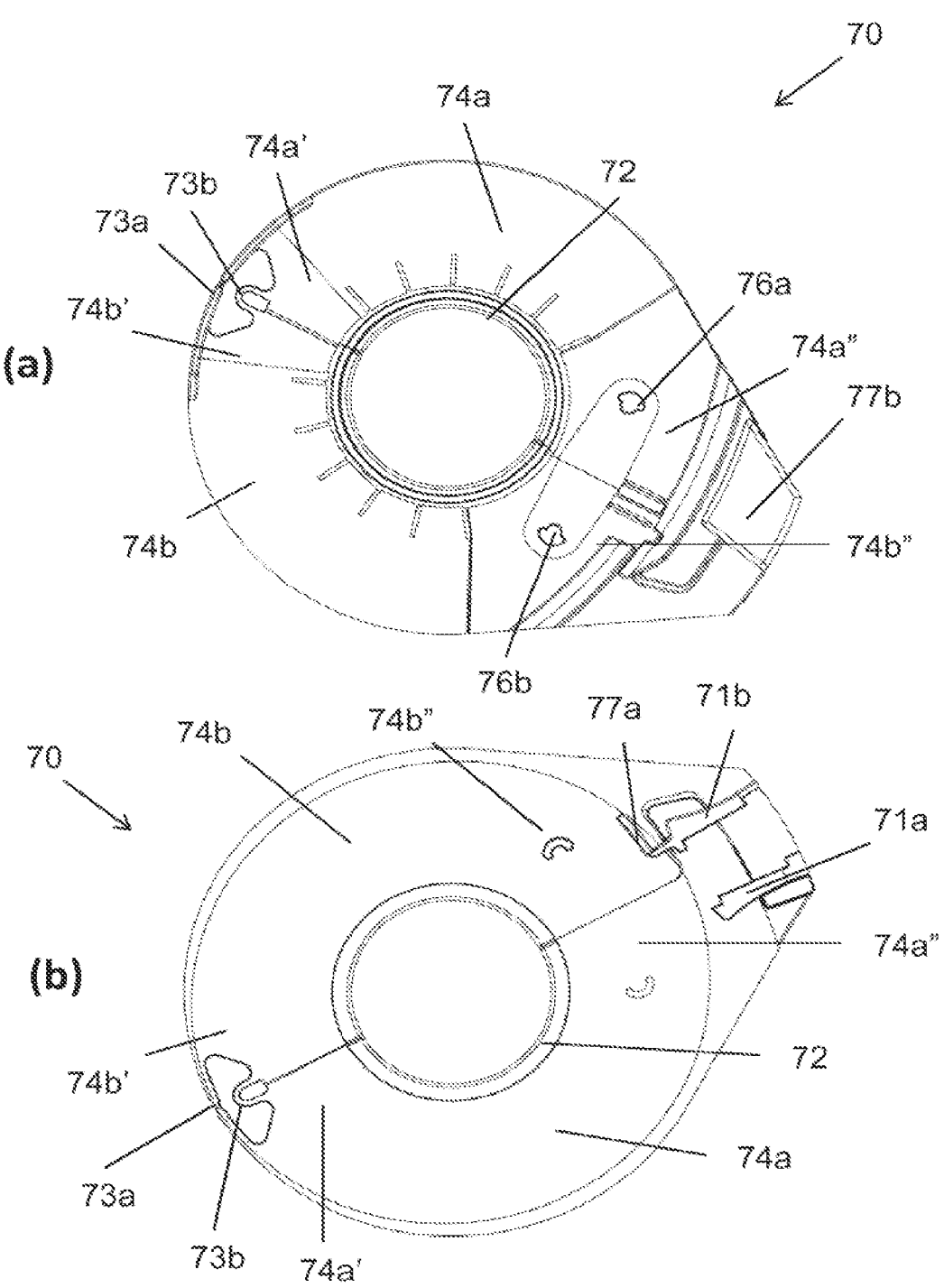
FIG. 29 shows (a) bottom and (b) top views of an embodiment of a connector in a closed configuration.
Figure 30:
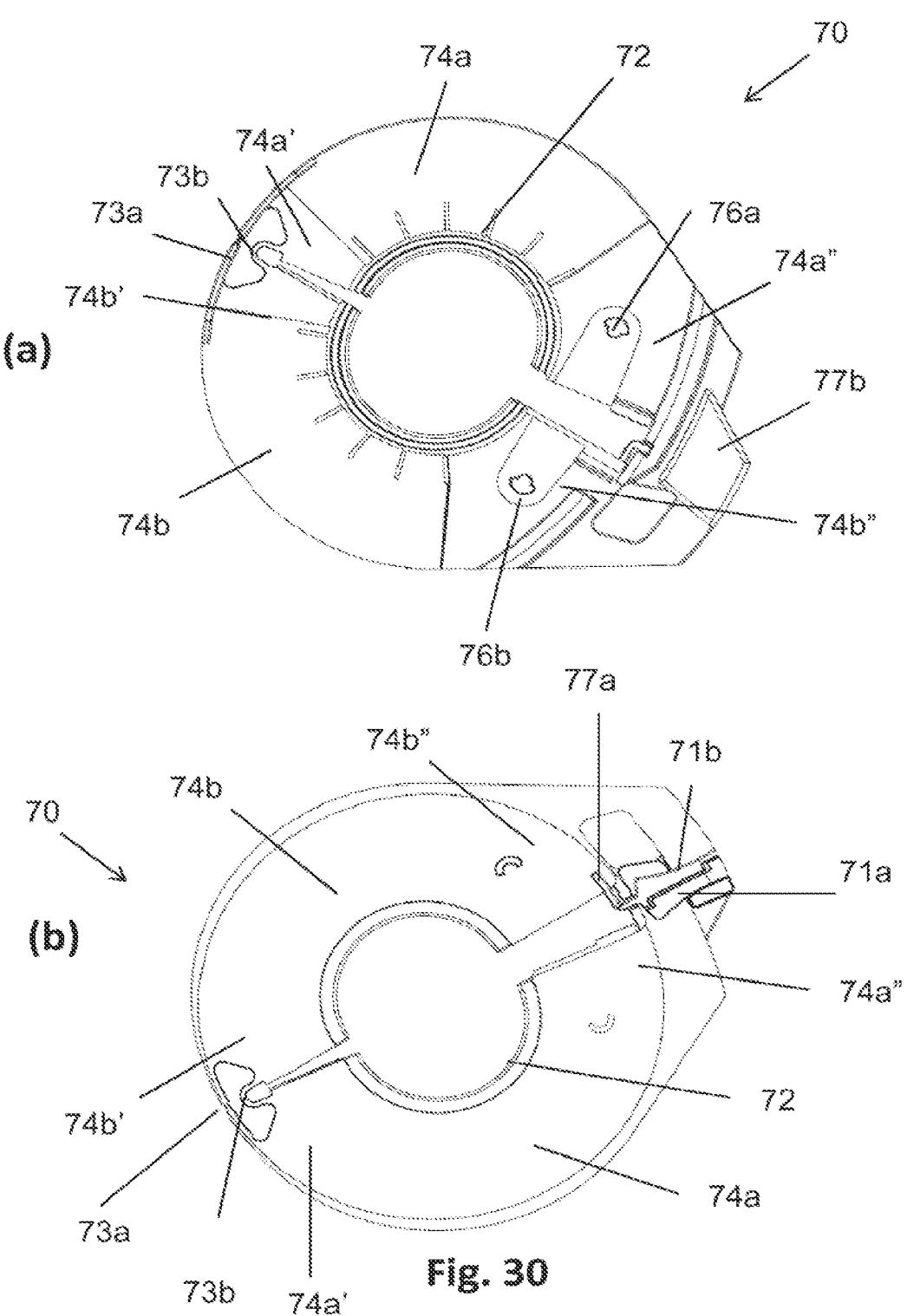
FIG. 30 shows (a) bottom and (b) top views of the connector of FIG. 29 in an open configuration.

FIGS. 29 and 30 show a connector 70 in closed and open configurations, respectively. The connector 70 is substantially ring-shaped and is formed of two relatively planar halves 74a and 74b. Each half 74a, 74b, has a joined end 74a', 74b' and a connecting end 74a" and 74b".

A device such as a sleeve, catheter or bag may be adhered to the upper surface of these halves 74a 74b.

A connecting edge 72 is provided around an inner circumference of the two halves 74a 74b. The connecting edge 72 is formed of a soft rubbery material and is sized and dimensioned so as to fit in and seal with the groove 14 in the lid (or in the groove 6 in an implant 1).

The two halves 74a, 74b are joined at their joined ends 74a', 74b' by a pair of relatively thin and flexible bending member 73a, 73b.

At each connecting end 74a", 74b", a squeezing member 71a, 71b is provided, which, when squeezed together, cause the connecting ends 74a", 74b" to move apart and the connector 70 to open. The squeezing members 71a and 71b slightly overlap the connecting ends 74b", 74a" to which they are not attached. In addition, a retaining member 77a, 77b is provided at each connecting end 74a", 74b", which also overlaps the other connecting end 74b", 74a". These overlapping features act to keep the two halves 74a, 74b in the same plane.

A further member 76a, 76b, is provided at each connecting end 74a", 74b'. These further members 76a, 76b project out of the plane of the connector 70 and have a flattened end part such that one or more elastic bands (not shown) can be placed around the further members 76a, 76b. The elastic bands are sized such that they act to keep the connector 70 in a closed position.

The same soft rubbery material that is provided along the connecting edge 72 is also provided along the joining edges of the connector 70 at the joined ends 74a', 74b' and connecting ends 74a", 74b" so that, when the connector 70 is closed, the two halves 74a, 74b are in sealing connection with each other.

The connector 70 is provided in a closed state as illustrated in FIG. 29. In order to attach the connector 70 to a lid 10, the connector 70 is opened by squeezing the squeezing members 71a, 71b together. This stretches the elastic band(s) and the two halves 74a, 74b of the connector 70 are opened (as shown in FIG. 30). The connector 70 is then placed around the groove 14 in the lid 10 (or around the groove 6 in an implant 1) and pressure on the squeezing members 71a, 71b is released such that the two halves 74a, 74b of the connector 70 are pulled back together by the elastic band(s) so that the connecting edge 72 is located in the groove 14 in the lid (on in the groove 6 in an implant 1), thereby holding the connector 70 in place.

In order to remove the connector 70 from a lid 10 or implant 1, the same procedure is performed again except that the connector 70 is removed from the lid 10 or implant 1, rather than being placed around it.

The connector 70 is manufactured by injection moulding. The two halves 74a, 74b of the connector 70 are injection moulded together in a first tool. Then they are placed in a second tool and the soft rubbery material is injection moulded on to them along the connecting edge 72 and joining edges between the two halves 74a, 74b.

The two halves 74a, 74b of the connector 70 are then connected together at their connecting ends 74a", 74b" by positioning the connecting end 74a", 74b" (partly) under their respective retaining members 77a, 77b. One or more elastic bands are then placed around the members 76a, 76b so that the connector 70 is ready for use.

Figure 31:
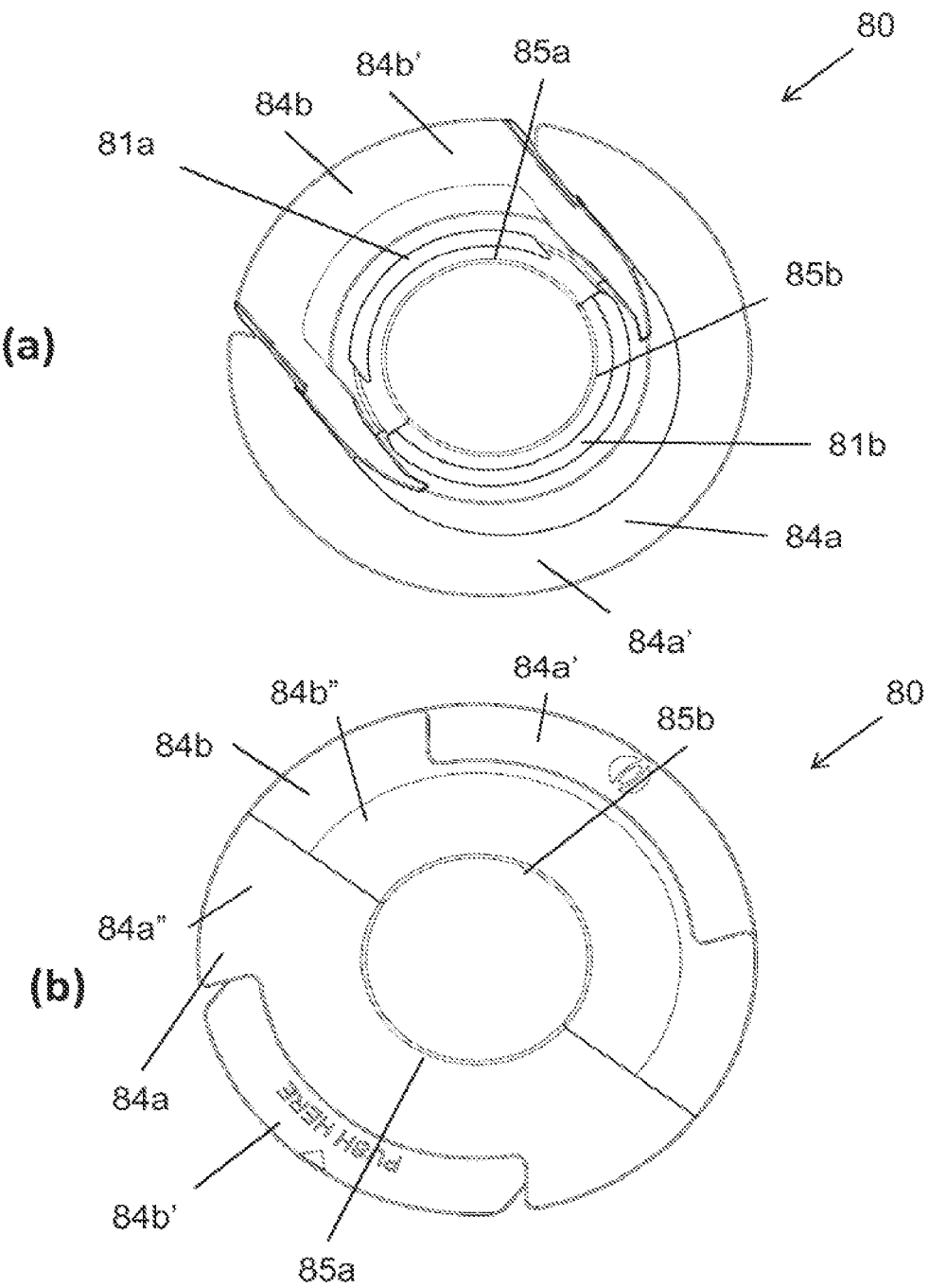
FIG. 31 shows (a) bottom and (b) top views of an embodiment of a connector in a closed configuration.
Figure 32:
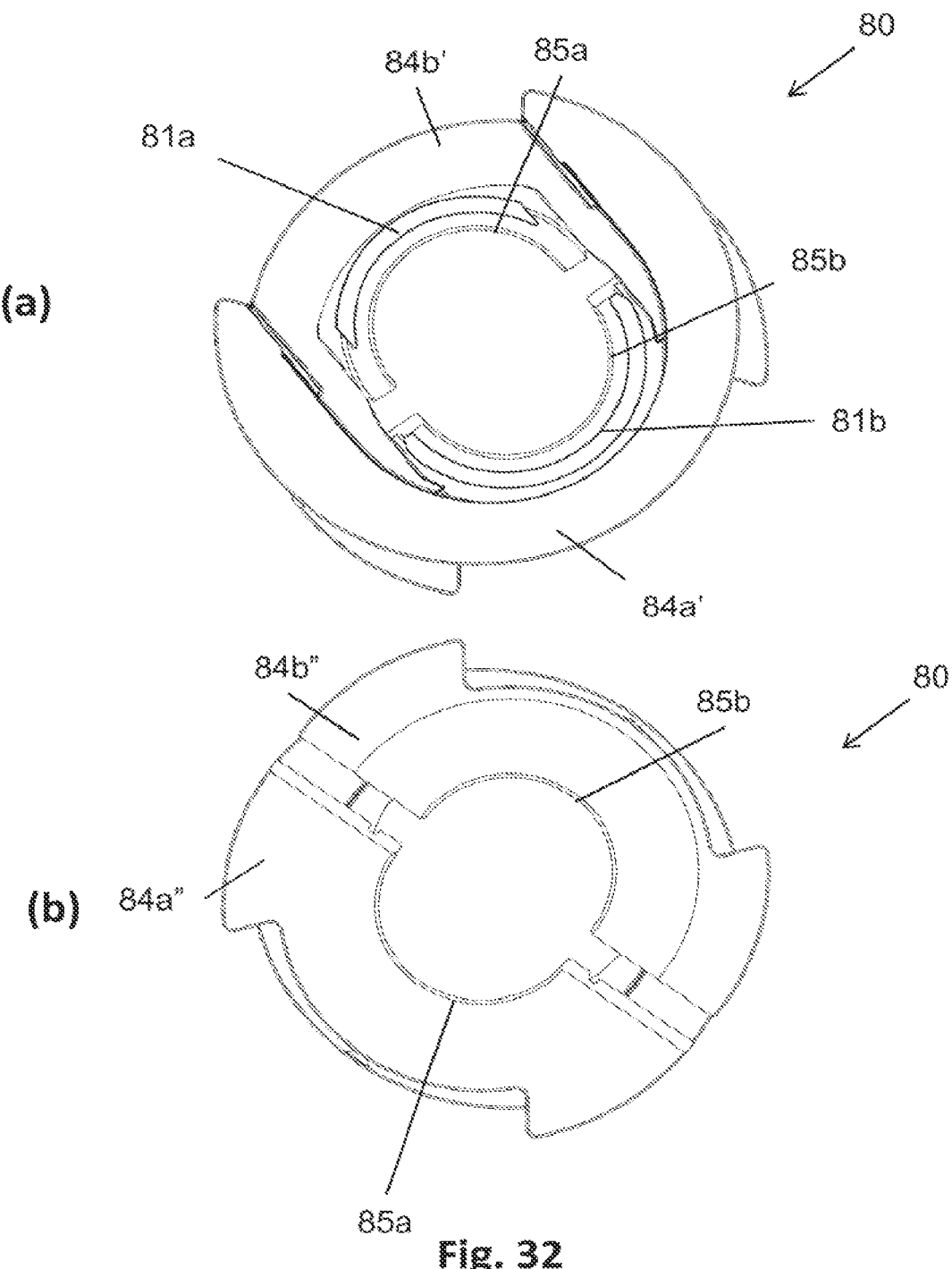
FIG. 32 shows (a) bottom and (b) top views of the connector of FIG. 31 in an open configuration.

FIGS. 31 and 32 show a connector 80 in closed and open configurations, respectively. The connector 80 is substantially ring-shaped and is formed of first and second relatively planar, overlapping, interlocking ring parts 84a and 84b.

A device such as a sleeve, catheter or bag may be adhered to the upper surface of these ring parts 84a, 84b.

The first ring part 84a is formed of an outer ring part 84a' and an inner ring part 84a". Similarly, the second ring part 84b is formed of an outer ring part 84b' and an inner ring part 84b". The two inner ring parts 84a" and 84b" are the same in size and shape and form the inner circumference of the connector 80. The two outer ring parts 84a' and 84b' form the outer circumference of the connector 80, with the outer ring part 84a' being larger and forming a greater part of that circumference than the outer ring part 84b'.

The inner and outer ring parts 84a', 84b', 84a", 84b" are interlocking in that that inner ring part 84a' of the first ring part 84a is located above the outer ring part 84b" of the second ring part 84b, and the inner ring part 84b' of the second ring part 84b is located above the outer ring part 84a" of the first ring part 84a. This interlocking feature helps to keep the two ring parts 84a, 84b together.

The inner ring parts 84a" and 84b" each have a retaining member 81a, 81b, respectively, around their inner circumference, around which an elastic band (not shown) is positioned. The elastic band acts to pull the ring parts 84a and 84b together across the diameter of the connector 80, and thereby keeps the connector 80 in a closed configura-tion, as shown in FIG. 31.

An inner groove (not visible in the figures) is provided on each side between the outer and inner ring parts 84a', 84a" of the first ring part 84a. Similarly, corresponding ridges (not visible in the figures) are provided on the inner surfaces of the inner ring part 84b" of the second ring part 84b. The ridges can move along inside the grooves and this allows the two ring parts 84a and 84b to move towards/away from each other. Similarly, the grooves and ridges also act to hold the two ring parts 84a, 84b together.

Connecting edges 85a, 85b are provided around the inner edges of the two inner ring parts 84a" and 84b". The connecting edges 85a, 85b are formed of a soft rubbery material and are sized and dimensioned so as to fit in and seal with the groove 14 in the lid (or in the groove 6 in an implant 1).

The same soft rubbery material that is provided along the connecting edges 85a, 85b is also provided along the joining edges of the interlocking ring parts 84a and 84b so that, when the connector 80 is closed, the two ring parts 84a and 84b are in sealing connection with each other.

The connector 80 is provided in a closed state as illustrated in FIG. 31. In order to attach the connector 80 to a lid 10, the connector 80 is opened by squeezing the two outer ring parts 84*a*", 84*b*" together. This causes the ridges to move along inside the grooves, stretches the elastic band, the inner ring parts 84*a*', 84*b*' move away from each other and the connector 80 is opened (as shown in FIG. 32).

The connector 80 is then placed around the groove 14 in the lid 10 (or around the groove 6 in an implant 1) and pressure on the two outer ring parts 84*a*", 84*b*" is relaxed or reduced such that the inner ring parts 84*a*', 84*b*' of the connector 80 are pulled back together by the elastic band so that their inner edges are located in the groove 14 in the lid (on in the groove 6 in an implant 1), thereby holding the connector 80 in place.

In order to remove the connector 80 from a lid 10 or implant 1, the same procedure is performed again except that the connector 80 is removed from the lid 10 or implant 1, rather than being placed around it.

The connector 80 is manufactured by injection moulding. The two interlocking ring parts 84*a* and 84*b* are injection moulded separately in their own first tools. Then they are each placed in their own second tools and the soft rubbery material is injection moulded on to them along the connecting edges 85*a*, 85*b* and the joining edges of the interlocking ring parts 84*a* and 84*b*.

The two interlocking ring parts 84*a* and 84*b* of the connector 80 are then slotted together and one or more elastic bands are then placed around the retaining members 81*a*, 81*b* so that the connector 80 is ready for use.

The connectors 60, 70, 80 are made of plastic, specifically polypropylene, with Mediprene® being used as the soft rubbery material. In any of the connectors 50, 60, 70, 80, instead of polypropylene, acrylonitrile butadiene styrene (ABS), polybutylene terephthalate (PBT) or polyoxymethylene (POM) could be used for increased rigidity.

When a connector 50, 60, 70, 80 is connected to a lid 10, the lid 10 cannot accidentally be removed from the implant 1, because the presence of the connector 50, 60, 70, 80 around the lid 10 will prevent the base 13 of the lid 10 from being stretched or bent into the widened state (with an enlarged opening 15) which is required for removal of the lid 10 from (or mounting of the lid 10 to) the implant 1.

The lid 10 and connectors 50, 60, 70, 80 are intended for ambulatory care and can be applied by either healthcare professionals or patients themselves.

The system consisting of the implant 1, lid 10 and connector 50, 60, 70, 80, together with a further device such as a sleeve, catheter or bag, prevents seepage and is intended to eliminate the need for constantly wearing an external appliance (e.g. pouch/bag) on the abdomen for collection of intestinal content.

After an implant 1 has been implanted into a patient, patients will typically have to use standard ostomy bags for an initial period of time before they can start using the lid 10. However, once the tissue is healed and fully integrated with the implant 1, the exterior end of the implant 1 can be closed with a lid 10.

Use of the lid 10 should be gradually introduced by momentary use over an acclimatisation period, the length of which may vary from patient to patient. During this acclimatisation phase, the lid 10 may be used for short periods, which are gradually increased in duration and frequency. Between lid uses, it is recommended to use ostomy bags. The lid 10 should not be used permanently before lid acclimatisation is completed.

As the lid 10 is used, the intestine gradually develops a natural reservoir 100 behind the implant 1. The development of this reservoir 100 means that the intestinal contents do not need to be emptied as often.

Once the acclimatisation phase has been completed, use of the lid 10 means that a patient usually no longer needs to use an ostomy bag during the daytime. However, it is in some cases still preferable to use an ostomy bag at night.

The length of time between emptying of the intestine varies from person to person, but the intestine normally needs to be emptied two to ten times a day.

The process for emptying the intestine is described below.

First, a connector 50, 60, 70, 80 is connected to the lid 10 and an irrigation sleeve is affixed to the connector 50, 60, 70, 80. The open (i.e. not affixed to the connector 50, 60, 70, 80) end of the irrigation sleeve is positioned over a toilet.

The hatch 12 of the lid 10 is then opened inside the sleeve. The opening of the lid 10 is performed from outside the sleeve to avoid soiling, i.e. the patent operates the lid 10 through the sleeve without directly touching the lid 10.

When the hatch 12 has been opened, the intestine can be emptied. In order to do this, the patient bends slightly forwards to empty all the contents of the intestine through the irrigation sleeve.

When emptying is completed, the hatch 12 is closed, the sleeve is then removed and disposed of, and the connector 50, 60, 70, 80 is removed and either rinsed for further use or also disposed of.

It can be convenient at this stage for a patient to replace the lid 10 with a second lid 10, and to rinse the first lid 10 ready for the next emptying.

The patient's skin, stoma and external surface of the implant 1 should be wiped clean, preferably with lukewarm running water, if available, before replacing the lid 10. Disinfectants should be avoided.

Should the emptying procedure require more length period of time, rather than an irrigation sleeve, an ostomy bag could be temporarily used on the skin around the implant 1, after removal of the irrigation sleeve and connector 50, 60, 70, 80, and possibly also the lid 10. Alternatively, an ostomy bag, rather than an irrigation sleeve, could be affixed to the connector 50, 60, 70, 80. In either case, when emptying is completed, the lid 10 should be closed from outside the bag before the bag is removed.

Once the lid 10 is in continuous use, it should be replaced every week for hygienic reasons. The connector 50, 60, 70, 80 should be replaced every day. Alternative embodiments of the lid and/or connector may require more or less frequent replacement.

Throughout this specification terms such as top/bottom/side/upper/lower are used. These are used for clarity and refer merely to the way in which the implant, lid and/or connector are typically viewed or considered (as shown in the figures unless otherwise indicated), i.e. with the external end of the implant at the top and the hatch of the lid opening upwards. However, of course, in use, the implant (and so therefore also the lid) may have different orientations and so parts referred to as top/bottom/side/upper/lower may of course have a different relative location.

The invention claimed is:

1. A connector for connection to an ostomy implant or to a lid for an ostomy implant, the connector forming an integrated structure disposed generally in a plane and being substantially ring-shaped, the connector comprising:

(i) an outer part, and (ii) an inner part formed from a material more flexible than a material of the outer part, the inner part being configured for sealing engagement with the ostomy implant or the lid;

wherein the connector comprises a connection surface for connection to a further device;

wherein the outer part comprises a plurality of tongues, each tongue projecting radially inwardly in said plane and having an inner end;

wherein the inner ends of the tongues together define an initial opening;

wherein the tongues are configured to flex resiliently from an original position in the plane of the connector to a deflected position extending out of the plane in response to an external force, thereby enlarging the initial opening during placement of the connector onto the ostomy implant or lid, and to resiliently return to the original position to engage a circumferential groove of the ostomy implant or lid so as to retain the connector in place during use; and wherein the inner part comprises a flexible sealing portion extending from radially outward of the inner ends of the tongues to radially inward of the inner ends of the tongues, the sealing portion being configured to bend to form a sealing engagement against a circumferential wall of the ostomy implant or lid.

2. The connector as claimed in claim 1, wherein the connection surface comprises a planar surface for attachment to a further device selected from the group consisting of an ostomy bag, an irrigation sleeve, and a catheter.

3. The connector as claimed in claim 1, wherein the tongues project radially inwardly over and under the flexible inner part, such that the connector is arranged to connect to the ostomy implant or lid from either side of the connector.

4. A device comprising the connector as claimed in claim 1 attached thereto.

5. The device according to claim 4, where the device is an ostomy bag, a catheter, or an irrigation sleeve.

6. A method of manufacturing a connector for an ostomy implant or for a lid for an ostomy implant, the connector being configured as in claim 1, the method comprising manufacturing the connector by injection moulding.

7. The connector as claimed in claim 1, wherein the tongues project radially inwardly into, through, over, and/or under the inner part.

8. The connector as claimed in claim 1, wherein the tongues extend towards, but not as far as, an inner edge of the inner part.

9. The connector as claimed in claim 1, wherein the initial opening extends through the connector.

* * * * *